US008595620B2

(12) United States Patent  
Larsen et al.

(10) Patent No.: US 8,595,620 B2
(45) Date of Patent: Nov. 26, 2013

(54) DOCUMENT CREATION AND MANAGEMENT SYSTEMS AND METHODS

(75) Inventors: Glen A. Larsen, Sandy, UT (US); Justin B. Rich, Salt Lake City, UT (US); Steven R. Mimnaugh, Sandy, UT (US); Dennis J. Wyman, Salt Lake City, UT (US); Robert K. Rothfeder, Sandy, UT (US)

(73) Assignee: Kwatros Corporation, Salt Lake City, UT (US)

( * ) Notice: Subject to any disclaimer, the term of this patent is extended or adjusted under 35 U.S.C. 154(b) by 378 days.

(21) Appl. No.: 12/891,740

(22) Filed: Sep. 27, 2010

(65) Prior Publication Data

US 2011/0078570 A1 Mar. 31, 2011

Related U.S. Application Data

(60) Provisional application No. 61/246,605, filed on Sep. 29, 2009.

(51) Int. Cl.
*G06F 17/24* (2006.01)

(52) U.S. Cl.
USPC .......................................................... 715/254

(58) Field of Classification Search
USPC .......................................................... 715/254
See application file for complete search history.

(56) References Cited

U.S. PATENT DOCUMENTS

| | | | |
|---|---|---|---|
| 6,477,491 B1 * | 11/2002 | Chandler et al. | 704/235 |
| 6,813,603 B1 | 11/2004 | Groner et al. | |
| 7,286,997 B2 | 10/2007 | Spector et al. | |
| 7,383,183 B1 | 6/2008 | Davis et al. | |
| 7,716,072 B1 * | 5/2010 | Green et al. | 705/3 |
| 2002/0046235 A1 * | 4/2002 | Foy et al. | 709/203 |
| 2002/0099717 A1 | 7/2002 | Bennett | |
| 2002/0188452 A1 | 12/2002 | Howes | |
| 2004/0193450 A1 | 9/2004 | Knapp | |
| 2006/0116908 A1 | 6/2006 | Dew et al. | |
| 2006/0197753 A1 * | 9/2006 | Hotelling | 345/173 |
| 2006/0212452 A1 | 9/2006 | Cornacchia | |
| 2006/0265249 A1 | 11/2006 | Follis et al. | |
| 2006/0277072 A1 | 12/2006 | Bell et al. | |
| 2007/0033535 A1 | 2/2007 | Cornacchia | |
| 2007/0081428 A1 | 4/2007 | Malhotra et al. | |
| 2008/0250070 A1 | 10/2008 | Abdulla et al. | |

FOREIGN PATENT DOCUMENTS

DE 10117319 9/2001
WO WO 2008/120146 10/2008

* cited by examiner

*Primary Examiner* — Doug Hutton, Jr.
*Assistant Examiner* — Tionna Smith
(74) *Attorney, Agent, or Firm* — Stoel Rives LLP; R. Whitney Johnson

(57) ABSTRACT

Systems and methods for document creation and management to facilitate creation of documents. An example document creation and management system is configured with an input component, a processing component, and a document creation component. A document creation and management systems can allow input of data in a customizable manner via talking (or recording), touching, typing, and/or clicking. A document creation and management system may use customizable templates, so that a user, for example a physician, may more efficiently enter and review data, such as data related to a patient encounter. A navigator may import information, such as formatting and structure information, from a template to guide a user as to the input to be provided to generate a document according to the template. Document entries may be automatically sent for processing, which may include editing, transcription, encryption, etc, in a parallel or serial fashion. For example, dictation information may be automatically transcribed and/or processed.

27 Claims, 16 Drawing Sheets

Jane Smith, MD175 West 200 South #4004Salt Lake City, UT 84101Phone: (801) 359-1621Fax: (801) 532-3900

Patient Name: Practice Patient 04MRN: 42345678DOB: 1988-03-20Gender: MALEDate of Visit: 2010-09-23Time of Visit: 02:00 PMTime of Arrival: pending

CHIEF COMPLAINT
Patient comes in with complaints of right ankle injury, pain and swelling.

HISTORY OF PRESENT ILLNESS
The patient is a 22-year-old male who presents with an ankle injury he sustained yesterday after dunking a basketball and coming down on another player's foot. He describes an inversion injury. He denies motor or sensory deficit of the affected extremity or any other injury. [Transcribed by EvolveMed]

PAST, FAMILY, AND SOCIAL HISTORY
Nursing Note: Reviewed.
Allergies: No known allergies to medications.
Medications: No medications are taken on a regular basis.
Immunizations: Relevant immunizations are current.
Previous Trauma: No significant previous trauma.
Surgeries: No previous major surgical procedures.
Previous Illnesses and Hospitalizations: No previous hospitalizations or significant illnesses.
Family History: No known significant family medical problems.
Social History: Denies tobacco, alcohol or drug use.

REVIEW OF SYSTEMS
Musculoskeletal: No other injury. No knee or proximal fibular pain.
Neurologic: Negative for weakness, numbness and tingling.
All Others Negative: All other systems are negative.

FIG. 10

DOCUMENT CREATION AND MANAGEMENT SYSTEMS AND METHODS

CROSS-REFERENCE TO RELATED APPLICATION

This application claims the benefit under 35 U.S.C. §119(e) of U.S. Provisional Patent Application No. 61/246,605, filed Sep. 29, 2009, which is hereby incorporated by reference herein in its entirety.

TECHNICAL FIELD

The present disclosure relates to information management systems and methods, and in particular to systems and methods for creating and managing documents.

BRIEF DESCRIPTION OF THE DRAWINGS

The present disclosure may best be understood by reference to the following description taken in conjunction with the accompanying drawing figures, in which like parts are referred to by like numerals:

FIG. 10 illustrates a patient interaction report (output document) generated by a creation and management system, according to one embodiment of the present disclosure.

DETAILED DESCRIPTION

Figure 1A:
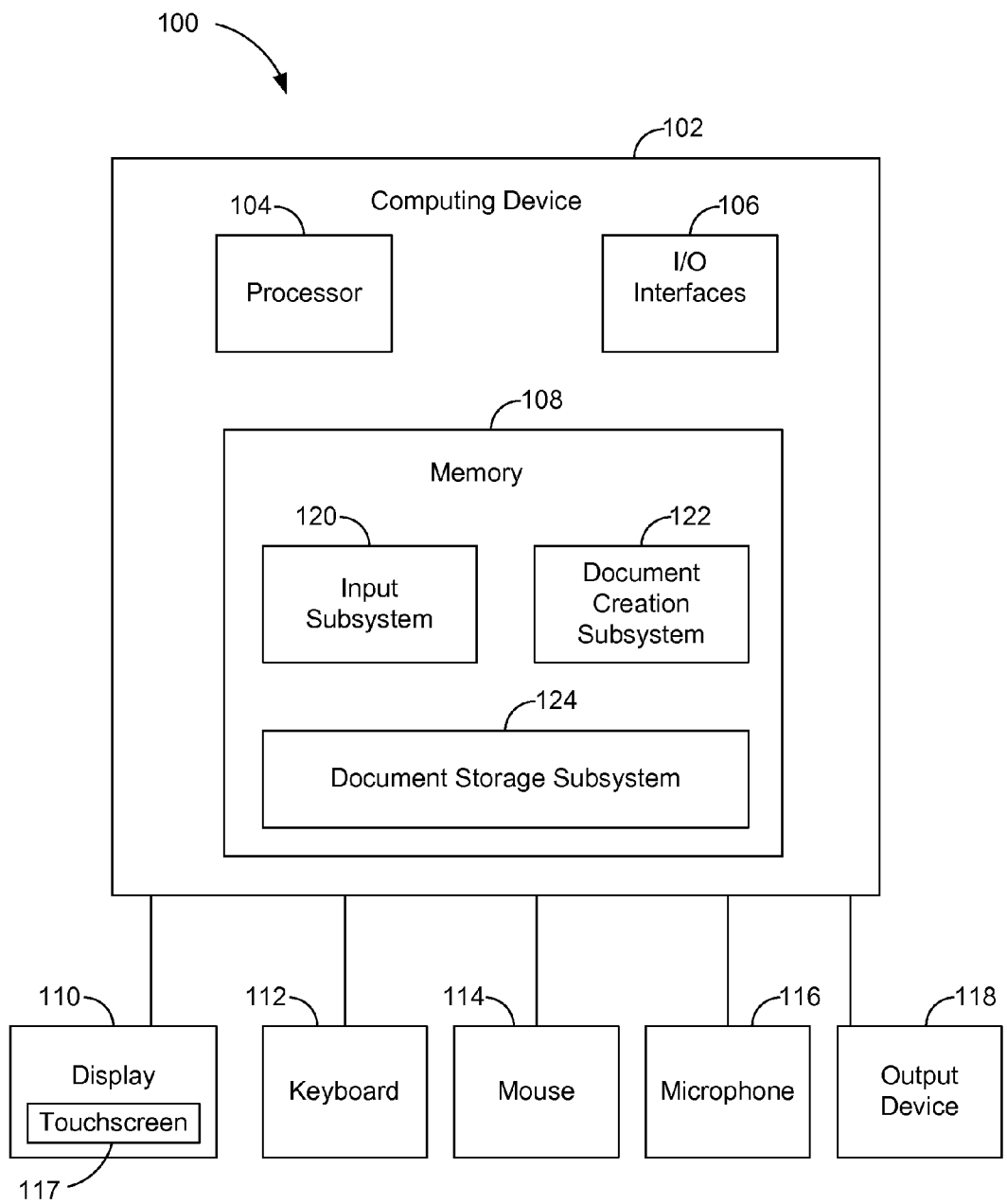
FIG. 1A illustrates a block diagram of a document creation and management system, according to one embodiment of the present disclosure.

Traditionally, medical records have been created by free-form handwriting or free-form dictation and medical transcription. Modernly, and especially since the implementation of the Centers for Medicare and Medicaid Services ("CMS") Evaluation & Management Services documentation guidelines (the "E&M Guidelines") in 1995, medical records have been created using traditional methods, plus a variety of newer methods, including: paper templates; digital dictation and transcription; templated dictation; speech recognition; and various other computer-generated or computer-assisted systems. Each approach has various disadvantages.

The majority of medical records created today are either hand-written paper records or free-form dictated and transcribed records. Presently, there is a strong push towards Electronic Medical Records (EMRs), which may include transcription, scanned paper records, and/or a myriad of computer generated records. Further, speech recognition software may be utilized to convert recorded speech into text. Computer generated records generally provide a methodology for the user to create a medical record with mouse-clicks and user-typing as a way to eliminate the transcriptionist labor component and to speed up final completion of the record. A shortcoming, however, of computer-generated systems that attempt to eliminate dictation is that, by causing the user to type or click-generate the record from predetermined choices, time is wasted and the record may lose certain nuance of the narrative. An improved document creation and management system, enabling multiple methods of input and entry creation to generate document content and improve time efficiency is desirable. Moreover, customization of the document creation process is desirable.

In one embodiment, a document creation and management system may be configured as a record creation system for creating a medical record. In this configuration, the document creation and management system may desirably capture physician input at the time of a patient encounter with suitable nuance and detail as desired. As will be described, the document creation and management system enables information regarding a patient encounter to be captured without imposing unnecessary sacrifice of a physician's valuable time and/or impairing the integrity of the patient encounter, for example by obligating the physician to repeatedly disengage from communication with the patient to enter information, or requiring the physician to spend additional time after-hours to complete a medical record.

In the field of medical records, freeform dictation is often preferred for effective and complete documentation of patient encounters. Products supporting freeform dictation, however, may be extremely costly, particularly for individual medical practitioners. Thus, systems and/or methods allowing a physician to reap at least some of the benefits of freeform dictation, without the attendant sizeable expense, are desired. For example, a document creation and management system allowing a physician to choose when and/or customize when (at which portions of a document it is appropriate or allowed) to talk, when to touch, when to click, and/or when to type can enable the physician to improve freedom for entering data into a medical record and improve cost control. Moreover, efficient creation of documentation associated with high complexity patient encounters, low complexity patient encounters, and/or moderate complexity patient encounters may thus be enabled.

Although the present disclosure provides a detailed description of a particular embodiment in the context of medical records, a person having ordinary skill in the art will appreciate that the invention is not so limited. The disclosure contemplates creation of records or documents in any field of endeavor involving document and/or information creation and/or management, including but not limited to law, architecture, engineering, software development, and/or other fields. The principles, features, systems, and methods discussed are merely indicative of exemplary applications and may be applied to other technical fields outside the medical field.

The subject matter may be described herein in terms of various functional components and processing steps. It should be appreciated that such components and steps may be implemented as any number of hardware or software components or combination thereof configured to perform the specified functions. For example, an exemplary embodiment may employ various graphical user interfaces, software components, and database functionality.

For the sake of brevity, conventional techniques for computing, data entry, data storage, networking, speech recognition, and/or the like may not be described in detail herein. Furthermore, the connecting lines shown in various figures contained herein are intended to represent exemplary functional relationships and/or communicative, logical, and/or physical couplings between various elements. As will be appreciated, however, many alternative or additional functional relationships or physical connections may be present in a practical implementation of a document creation and management system or method.

The present disclosure relates generally to information management, and to methods and systems for creating documents via predefined and/or customizable input components, tools, and techniques. Various example embodiments provide systems and processes for creating a document in a particular technical field, for example via input through customized clicking, touching, talking, and/or typing. Moreover, additional exemplary embodiments may provide systems and processes for creating a medical record, for example via input through customized clicking, touching, talking, and/or typing. A document creation and management system may be any system configured to facilitate data input to create a document.

A document, as the term is used herein, may refer to any collection of data or information having a defined organization. The data of a document may include content and the organization of the content may be defined by formatting rules. Although a document may encompass data or information printed on a paper, the term document is broader and encompasses any association of stored content, including content stored electronically or stored in a computer readable storage medium, and formatting rules specifying the presentation of the content. A document may further include other components such as headers, footers, disclaimers, tracking information, author information, security settings, and processing rules, some of which may be stored as entries and some of which may be stored in an alternative manner.

According to one embodiment of the present disclosure, a document may be preliminary or finalized. A preliminary document may be considered a work in progress, and can be modified, edited, changed, and the like. Content may be added and formatting of the content may be changed. In one embodiment, a finalized document cannot be modified, edited, changed, or the like, and remains in a permanently fixed state. In other embodiments, a finalized document may need to be unfinalized before changes can be made.

An output document is a form of document in which the content of a document is presented according to the associated formatting rules—i.e., a presentation of a document. An output document may be presented in any suitable format, including paper or electronic formats. An output document may be preliminary or finalized. For non-visual data contained in a document, an output document may present an icon or other indication that the non-visual data is embedded in the document. The icon may be positioned in the document according to the formatting rules and structure of the document.

The content of a document, according to the present disclosure, may be made up of one or more discretely stored entries. The term "entry" as used herein refers to any data, including but not limited to text, image data, audio data, and/or video data, that can be entered into or used to create the contents of a document. An entry may include one or more other entries. For example, an entry may include both text and an audio component. The text may be composed as a discrete entry and the audio may be composed as a discrete entry, and then the two entries may be combined in a new entry. In one embodiment, the text may be a preconfigured label or description of the audio entry. In another embodiment, the text may be a transcription of the audio entry. As another example, an entry may include both text and an image. The text may be composed as a discrete entry and the image may be composed as a discrete entry, and then the two entries may be combined to form a new entry. An entry may also include another document. In this manner, a document can be inserted into another document.

FIG. 1A illustrates a block diagram of a document creation and management system 100, according to one embodiment of the present disclosure. The system 100 may include a computing device 102 having a processor 104, input and output interfaces 106, a memory 108, a display 110, various input devices including but not limited to a keyboard 112, a mouse 114, a microphone 116, and a touchscreen 117 of the display 110, and an output device 118 such as a printer. The document creation and management system 100 may further include a number of components such as an input subsystem 120, a document creation subsystem 122, and a document storage subsystem 124. In the illustrated embodiment, these components may be modules stored in the memory 108. In one embodiment, one or more of these and other components of memory (the input subsystem 120, the document creation subsystem 122, the document storage subsystem 124, etc.), or combinations thereof, may be implemented as document creation software. In another embodiment, one or more of these components may be implemented in hardware. In still another embodiment, one or more of these components may be implemented in hardware and software. In still another embodiment, one or more of these components may be external to the document creation and management system 100 (see, e.g., FIG. 1B).

The input subsystem 120 may be configured to facilitate input of data to create a document. The input may be, for example, data entered by a user. The input subsystem 120 may comprise any suitable components, hardware, software, templates, and/or the like or combinations thereof, configured to facilitate the input of data. In the illustrated embodiment, the input subsystem 120 may comprise one or more software modules configured to present a set of user interfaces and/or input controls for receiving input in a variety of ways. For example, the input subsystem 120 may comprise a user interface providing a click input control interface configured to receive data input via mouse click, a touch input control configured to receive data input via touch, a type input interface configured to receive data input via keyboard strokes, a recorder input control configured to receive data input via a microphone, test and/or diagnostic equipment, and/or monitoring equipment (e.g., patient monitoring equipment), and so on. The input subsystem 120 may also comprise suitable components allowing a user to switch between input methods with a reduced level of disruption. For example, the input subsystem 120 may be configured to enable a user to input data in a first manner via a first interface, and then immediately begin inputting data in a second manner via a second interface.

The input subsystem 120 may also be customized, as desired. For example, the input subsystem 120 may be configured to support additional input methods, disable certain input methods, alter input configuration and/or formatting, permit simultaneous input of data via multiple input methods, and/or the like. Moreover, the input subsystem 120 may further be configured with any suitable menus, controls, feedback components, graphical user interfaces, and/or the like, in order to facilitate entry of data by a user.

The input subsystem 120 may be further configured to facilitate creation of templates to guide the input of data. The template creation components of the input subsystem 120 may be separate from the data input components. For example, template creation and/or editing may be accessed via different interfaces and/or paths and/or may require different access permissions. Alternatively, template creation and editing may be integrated with data input, such that, for example, template creation components can be accessed via the same paths and/or with the same permissions as data input and a template could be created or modified concurrently with data input. In one embodiment, the template creation/editing components of the input subsystem 120 may comprise a template editor, which may be implemented as one or more software modules configured to present a set of user interfaces and/or input controls for creating and editing a template. The template editor may allow a user to add categories and sub-elements of categories to specify the input to be gathered to generate a document according to the template. The template editor may present the categories and sub-elements as an expandable tree structure. The input subsystem 120 is discussed below in greater detail with reference to FIGS. 3A-3C.

The document creation subsystem 122 is configured to create a document using at least a portion of the input received via the input subsystem 120. In particular, the document creation subsystem 122 uses entries composed by the input subsystem 120 to generate a document. The document creation subsystem 122 may comprise hardware, software, algorithms, macros, templates, and/or the like, or combinations thereof, configured to generate a document using entries composed by the input subsystem 120. In the illustrated embodiment, the document creation subsystem 122 may comprise one or more software modules configured to perform one or more operations on entries in order to incorporate input data into the content of a document. The operations may be predefined by formatting rules, security rules, processing rules, and the like.

The document creation subsystem 122 may also perform one or more operations to produce an output document (i.e., the content of a document presented according to associated formatting rules). According to one embodiment, an output document may present only the content of a document formatted according to associated document formatting rules. An output document may also present all information, headers, footers, layout, formatting, sections, summaries, and/or other suitable document components. For example, an output document may comprise a presentation of a medical record document having at least one of physician information, patient information, history information, diagnostic information, symptom information, treatment information, and/or the like contained therein. The document creation subsystem 122 may comprise and/or interact with the display 110 and/or the output device 118 to present an output document.

The document storage subsystem 124 may be configured to store documents. The document storage subsystem 124 may store discrete document entries and store documents as an association of discretely stored entries. In one embodiment, the document storage subsystem 124 may be implemented as a relational database. As will be appreciated, however, the document storage subsystem 124 may be implemented in any manner suitable for storing discrete entries and associating groups of entries that form the content of a document. Moreover, as can be appreciated, in another embodiment, the document storage subsystem 124 may be embodied in a separate device (see, e.g., FIG. 1C). In one embodiment, the document storage subsystem may also include document templates, to guide user input to generate documents. The templates may also provide, among other things, formatting rules and processing rules for the document, which may affect a document's formatting, arrangement, and structure. The templates may be defined by user interaction with the input subsystem 120. Alternatively, the templates may be predefined externally and loaded into the system 100B. The templates may specify the formatting of a document (e.g., the arrangement of entries within the document, margins, page orientation, type face, bold, underlining, italics, etc.). The templates may also specify the formatting of particular entries (e.g., type face, bold, underlining, italics, etc.).

Figure 1B:
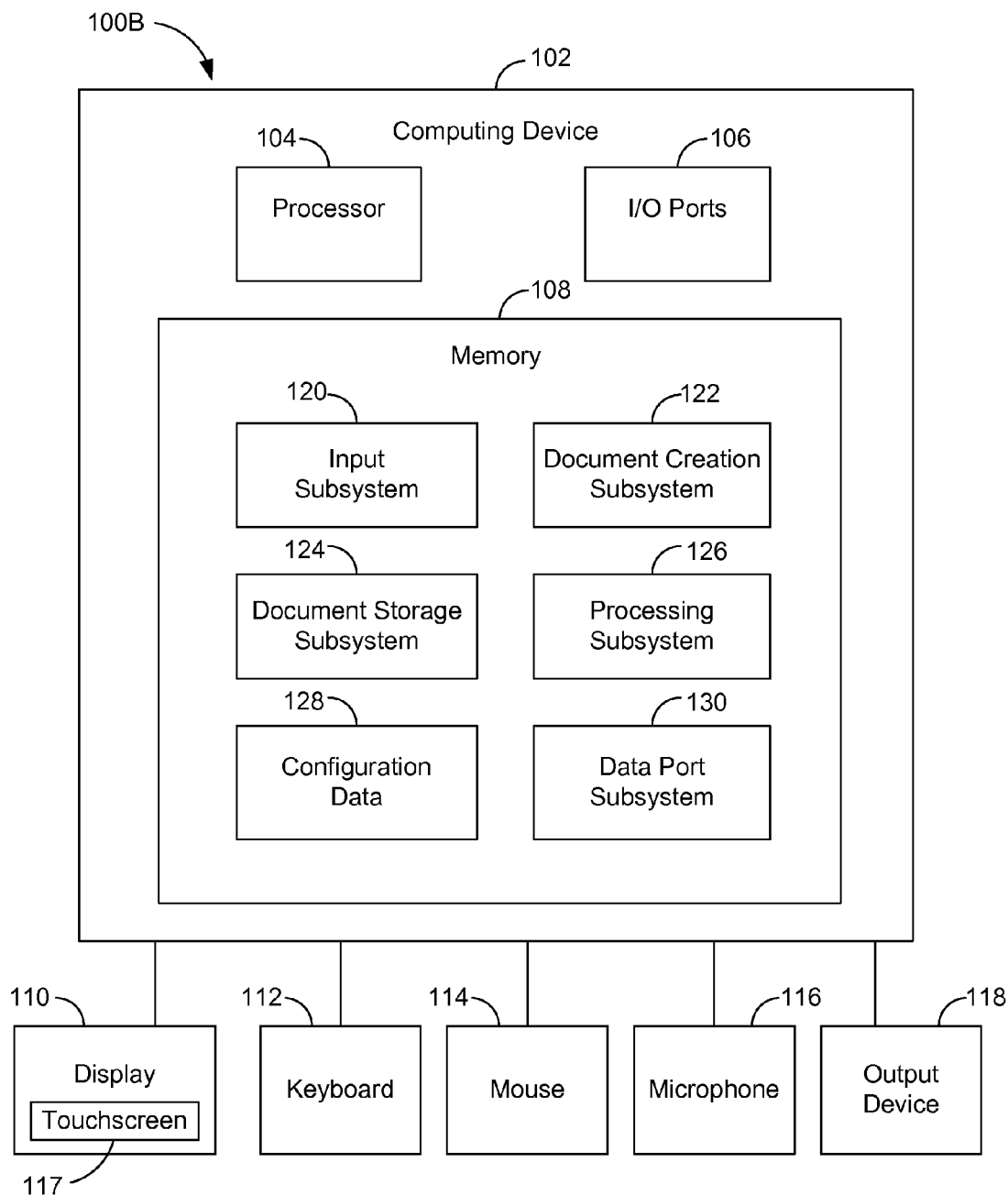
FIG. 1B illustrates a block diagram of a document creation and management system, according to another embodiment of the present disclosure.

FIG. 1B illustrates a block diagram of a another embodiment of a document creation and management system 100B. The system 100B may include the same components as system 100, as described above with reference to FIG. 1A, and may further include additional components. Specifically, the system 100B of FIG. 1B further includes a processing subsystem 126, configuration data 128, and a data port subsystem 130.

The processing subsystem 126 may include various functions for processing documents and/or entries of documents, including but not limited to formatting, merging, parsing, transcription (e.g., such as transcribing dictated audio input), translation of text in a foreign language, editing, spell-checking, encryption, summarizing, and/or the like. For example, the processing subsystem 126 may include a speech-recognition component configured to facilitate speech-to-text machine transcription of dictation audio input (also referred to herein as a "dictation snippet," to distinguish from non-dictated audio input). The processing subsystem 126 may also include an optical character recognition (OCR) component to, for example, provide electronic translation of image input containing handwritten, typewritten or printed text into machine-encoded text. The processing subsystem 126 may also include a machine translation component to translate text in one language into text of another language. The processing subsystem 126 may further include a spelling and/or grammar checker. The processing subsystem may further include an encryption component to provide encryption of sensitive information in an entry. As can be appreciated, some processing functions may be performed internally, such that the processing subsystem 126 may be a part of the document creation and management system 100B, while some functions may be better performed by a third-party, external to the document creation and management subsystem. Accordingly, the processing subsystem 126 may be embodied in a separate device (see, e.g., FIG. 1C).

The configuration data 128 may comprise user profile information, such as user login and password information. The configuration data 128 may store data to administer the system. In another embodiment, the configuration data 128 may include templates, formatting rules, and the like that may affect a document's formatting, arrangement, structure and the like. The templates may be defined by user interaction with the input subsystem 120. Alternatively, the templates may be predefined externally and loaded into the system 100B. Configuration data 128 may specify the formatting of a document (e.g., the arrangement of entries within the document, margins, page orientation, type face, bold, underlining, italics, etc.). Configuration data 128 may also specify the formatting of particular entries (e.g., type face, bold, underlining, italics, etc.).

The data port subsystem 130 may provide data communication services between various other components of the document creation and management system 100B. For example, the data port subsystem 130 may receive composed entries from the input subsystem 120 and communicate the entries to the document creation subsystem 122 to be incorporated into the content of a document. Similarly, the data port subsystem 130 may communicate formatting rules for that document from the input subsystem 120 to the document creation subsystem 122. The data port subsystem 130 may also communicate the document to the document storage subsystem 124 for storage of the document. The data port subsystem 130 may also communicate the document and/or entries of the document to the processing subsystem 126 and in turn receive the document back from the processing subsystem 126 after processing. The data port subsystem 130 may enable different components of the system 100 being physically positioned on different machines and/or hardware, as described below with reference to FIGS. 1C, 2, and 11.

Figure 1C:
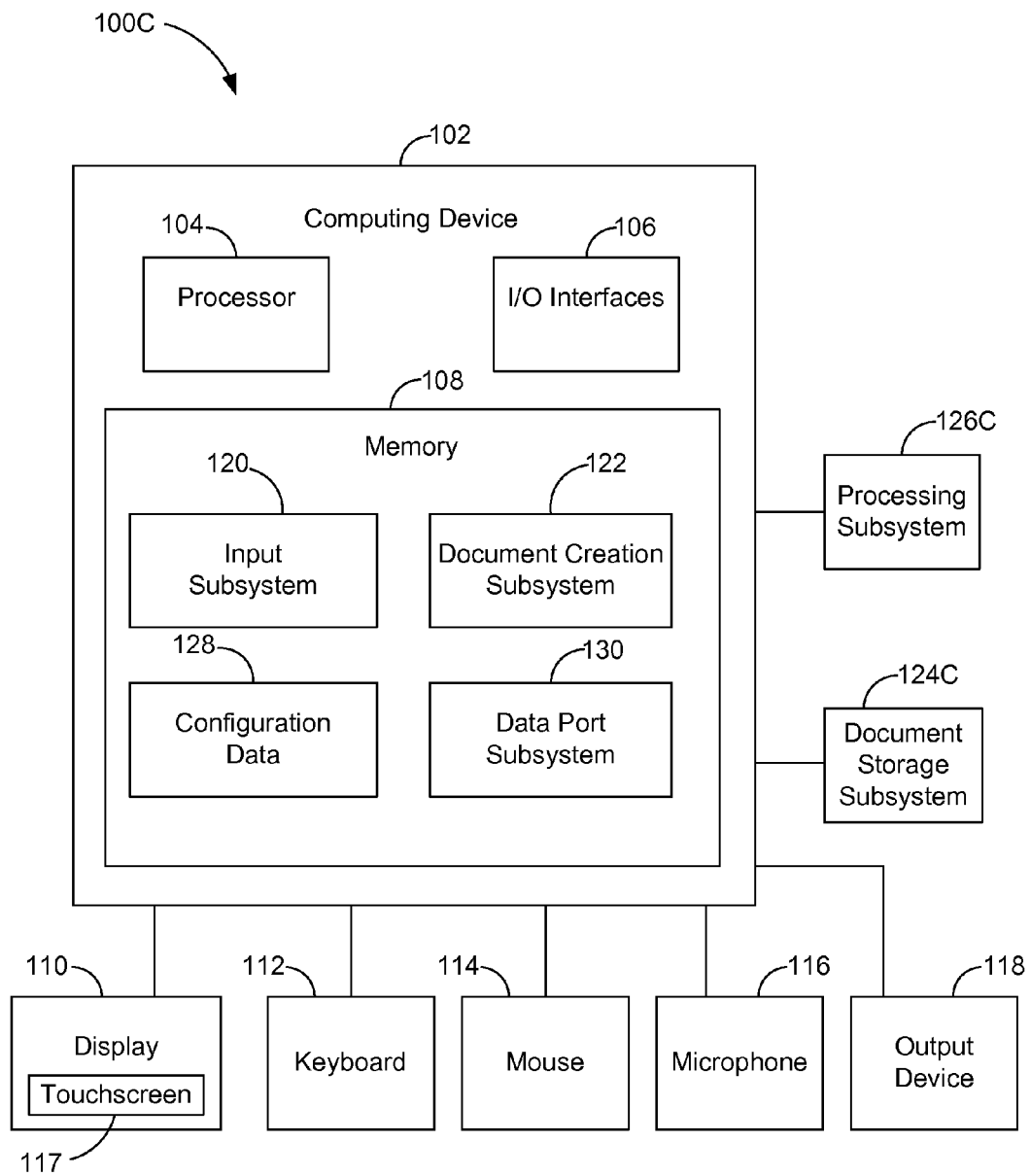
FIG. 1C illustrates a block diagram of a document creation and management system, according to another embodiment of the present disclosure.

FIG. 1C illustrates a block diagram of another embodiment of a document creation and management system 100C in which the processing subsystem 126C and the document storage subsystem 124C are separate from the computing device 102. The system 100C demonstrates that the processing subsystem 126C may be embodied in a different computing device and/or a third-party entity. For example, the processing subsystem 126C may include a transcription service that may provide transcription of dictation snippets. The transcription service may be a third-party, or otherwise external to the document creation and management system 100C. The system 100C of FIG. 1C also demonstrates that the document storage subsystem 124C may be embodied in a different device and/or a different entity. For example, the document storage subsystem 124C may comprise a database server machine separate from the computing device 102.

Figure 2:
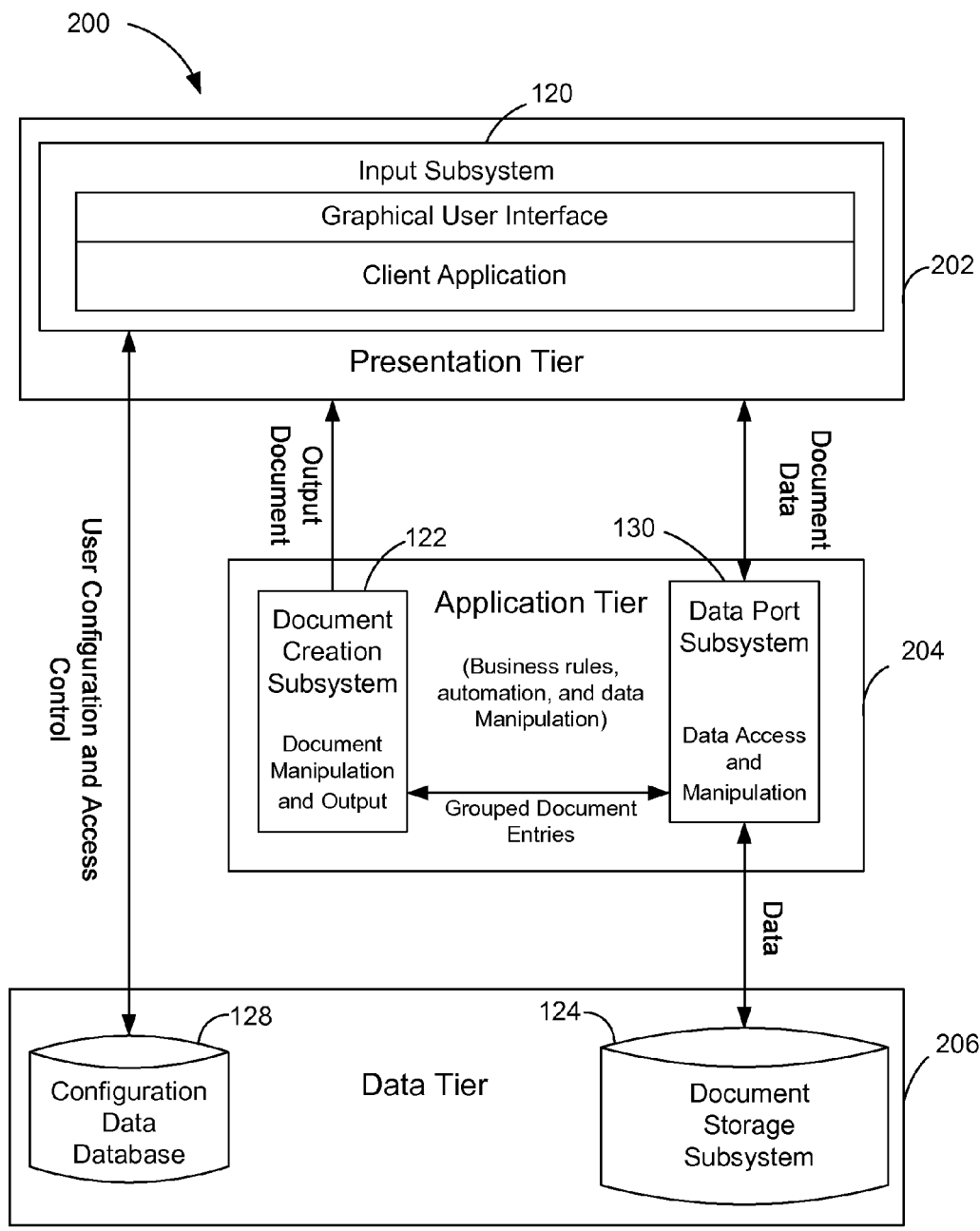
FIG. 2 illustrates another block diagram of a document creation and management system organized into multiple functional tiers, according to one embodiment of the present disclosure.

FIG. 2 illustrates block diagram of a document creation and management system 200 organized into multiple functional tiers. A first or "presentation" tier 202 may include the input subsystem 120. In one embodiment, the presentation tier 202 may comprise a client application (e.g., a web-based application), with an interactive graphical user interface. The presentation tier 202 may be operative on a web server and/or a client computing device. A second or "application" tier 204 may include the document creation subsystem 122 and the data port subsystem 130. The application tier 204 may enable automation, data retrieval and/or manipulation, and implementation of customized processing rules. The application tier 204 may be operative on an application server. Although not shown, the application tier 204 may also include a processing subsystem 126 (see FIGS. 1A-C). Alternatively, a processing subsystem may be external to the system 200. A third or "data" tier 206 may include a configuration database, including configuration data 128 and a document storage subsystem 124. The data tier 206 may enable storage and/or retrieval of data, including documents and their respective entries. The data tier 206 may be operative on or within a database server. In certain embodiments, data storage is isolated from other tiers in order to obtain improved security, scalability, and performance. Data may be input, retrieved, modified, and/or the like at any tier and/or via suitable processes.

Figure 3A:
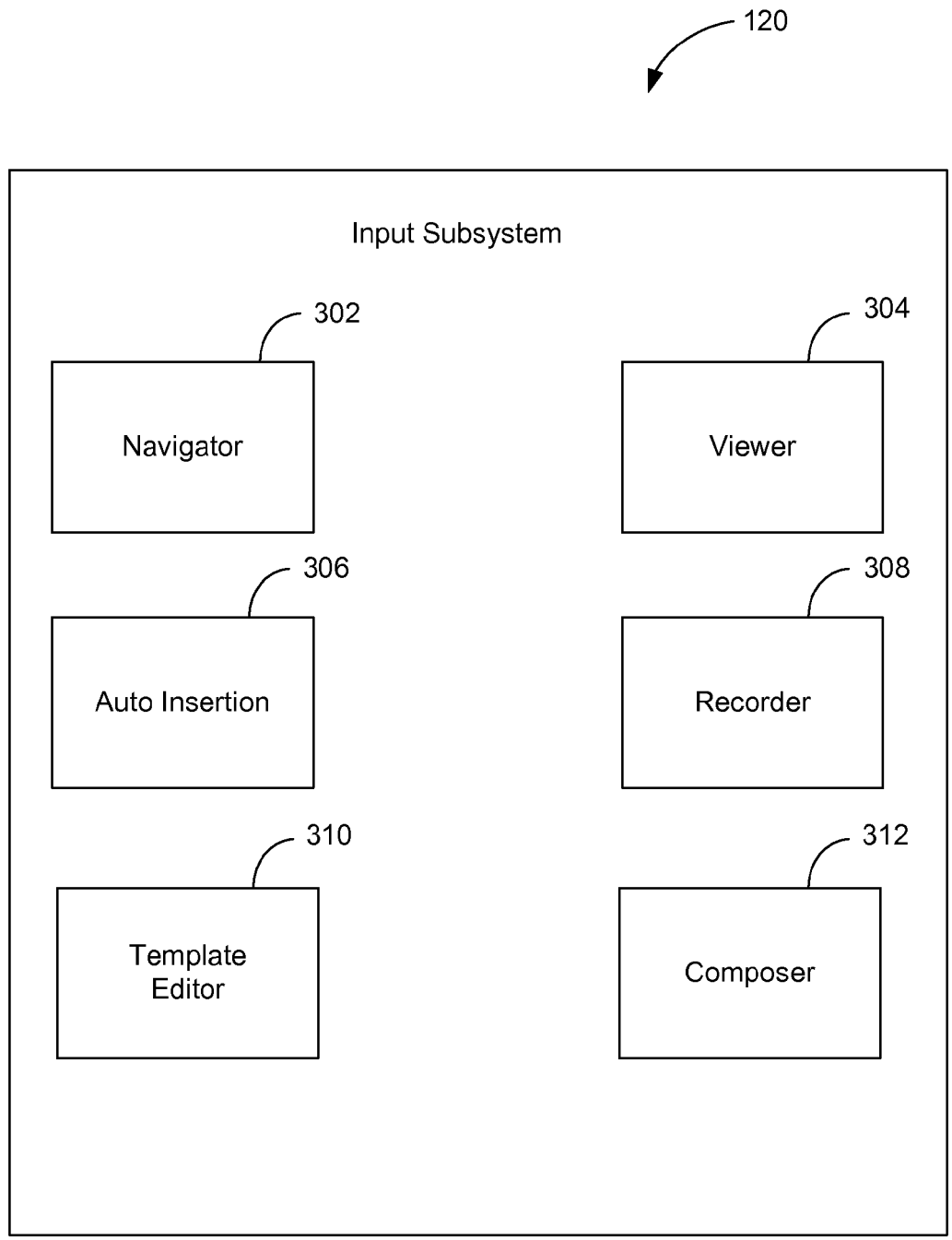
FIG. 3A illustrates a block diagram of an input subsystem of a document creation and management system, according to one embodiment of the present disclosure.

FIG. 3A illustrates a block diagram of an input subsystem 120 of one embodiment of a document creation and management system. The input subsystem 120 may comprise a user interface 300 (see e.g., FIG. 3B) and include one or more components to provide one or more user interfaces and/or input controls. The user interfaces and input controls may present data and receive input in a variety of ways. In the illustrated embodiment, the input subsystem 120 may include a navigator component 302, a viewer component 304, an auto-insertion component 306, a recorder input component 308, a composer component 312, and a template editor component 310.

The navigator component 302 (or simply "navigator") may be configured to provide a guide and structure for collection of input. The navigator component 302 may further be configured to guide, prompt, and or structure the composition of entries to create the content of a document. For example, the navigator component 302 may provide prompts configured to guide a user's thought process of document creation. In one embodiment, the prompts may be configured to be personalized (or otherwise customized) to a particular user, and substantially mirror that particular user's thought process. The navigator component 302 may be configured based on the configuration data 128 (FIG. 1B). For example, the prompts of the navigator component 302 may be provided by the configuration data. In one embodiment, the configuration data 128 may be a predefined template. The template may define formatting rules, including organizational and structural information for formatting a document. The template may further define entry formatting for individual entries, including but not limited to font, bold, italics, highlighting, and the like. The navigator component 302 may extract formatting information to configure a navigator user interface to guide and structure collection of input to create the content of a document.

The viewer component 304 (or simply "viewer") may provide a real-time "what-you-see-is-what-you-get" (WYSIWYG) view of an output document (i.e., a presentation of the content, or entries, of a document formatted according to associated formatting rules). In other words, the viewer component 304 may present an output document containing all entries and formatted according to any applicable formatting rules. The viewer component 304 may enable a user to identify gaps in the document and/or visually assess progress toward completion of the document. For data that may not easily be presented visually (e.g., a dictation snippet), the viewer may display an icon to indicate that the data is embedded and available. If the non-visual data is converted to visual data (e.g., a dictation snippet may be transcribed), the viewer may present both the visual data and an icon representing the non-visual data.

The auto-insertion component 306 may automatically compose preconfigured data into an entry of a document, in response to activation or manipulation of one or more input controls. The auto-insertion component 306 may enable a user to quickly and efficiently enter preconfigured data by automatically composing an entry with the preconfigured data, in response to, for example, a mouse click or a touch. Moreover, the preconfigured data may be customized, or otherwise preconfigured, according to an appropriate category of an entry. For example, a click input control may compose preconfigured data into an entry in response to user activation or manipulation. As another example, a touch input control may also compose preconfigured data into an entry in response to user activation or manipulation of the touch input control.

An example of a situation where the auto-insertion component 306 can prove useful is in the medical records context. As part of creating a medical record of an encounter with a patient, a physician, for example, is expected (or required) to record various aspects of the encounter, such as for example the status of a series of vital signs. In most patient encounters, many of these vital signs of the patient are normal. Nevertheless, these "normals" (i.e., normal status or result of any particular medical examination) must be recorded and typically a mere entry that the vital is "normal" is not sufficient (e.g., "heart rate is normal" or "allergies normal" would be insufficient). The physician may be expected to describe what "normal" is. For example, an physician may handwrite in the chart that "patient's heart rate is normal between 60 and 100 beats per minute" and that "the patient has no known allergies to medications". Writing this type of simple yet relatively lengthy statement for each normal, for repeated patient encounters can be time consuming. The auto-insertion component 306 may enable "normals" to be preconfigured and composed into an entry with the click of a mouse or a simple touch. A click input control (and/or touch input control) can be provided for each category or sub-element of an entry in a document (e.g., for each vital sign a physician must check for each patient encounter) and the preconfigured data can be customized for the particular associated category. For a "vital signs" sub-element of the Physical Exam category of entry in a medical record document, data to be auto-inserted by the auto-insertion component could be preconfigured to be the text "patient's heart rate is normal between sixty and one hundred beats per minute". Similarly, for an "allergies" sub-element of the Past Medical History category of entry in a medical record document, data to be auto-inserted by the auto-insertion component 306 could be preconfigured to be the text "the patient has no known allergies to medications." In this manner a physician can quickly and efficiently record "normals" in a customized way and according to the physician's personal preference, and pause to provide customized or different data only where a vital sign deviates from normal. As can be appreciated, the preconfigured data of the auto-insertion component 306 can be any form of data, and is not limited to text. For example, an electronic recording of a patient's blood pressure measurement may be auto-inserted as part of an entry for an entry relating to a "vital signs" sub-element of the Physical Exam category.

The recorder input component 308 (or simply "recorder") may be configured to record data to compose into an entry of a document. The recorder 308 may record dictation (spoken audio), allowing, for example, a doctor to dictate an aspect of a medical record document. A recording of dictation may be referred to herein as a dictation snippet. The recorder 308 may also be configured to record other forms of audio, such as audio of biological processes (e.g., the heartbeat of a fetus, a heart murmur, breathing of pneumonia infected lungs, etc.). The recorder 308 also may be configured to record video, such as for example an ultrasound or an endoscopy. The recorder 308 may also be configured to record biological process monitoring, such as for example monitoring of heart rate, respiratory rate, blood pressure, labor contractions, and the like. The recorder 308 also may be able to record any sort of testing or diagnostic monitoring system output. The recorder also may be able to record global positioning system (GPS) information. In short, the recorder 308 may be configured to record any form of data susceptible to being recorded.

The composer component 312 (or simply "composer") may be configured to receive and compose typed text into an entry. Upon activation of a type input control, the composer 312 may launch, providing a user an interface into which text can be typed by a user. In one embodiment, the composer 312 may directly enable activation of the recorder 308 to record input to compose into an entry and also enable activation of the auto-insertion component 306 to auto-insert data to compose into an entry. In other words, from the composer component 312 a user may be able to provide data input via various methods, including but not limited to typing text, auto-inserting preconfigured data with a click or touch, and recording data via the recorder 308. In this manner, the composer 312 may provide increased flexibility and options for providing input data to compose into an entry of a document.

In one embodiment, the composer 312 may provide preconfigured data upon launch to guide the generation of typed text. For example, the composer 312 may launch and pre-insert a text sentence with a series of blank spaces to be filled in with typed text. A user may be able to tab between the blank spaces and provide typed, recorded, and/or additional auto-inserted text to fill in the blank. As another example, the composer 312 may launch with a plurality of preconfigured data input options, any of which can be entered, for example, by selecting a particular data input option.

In another embodiment, the composer 312 may further comprise a natural language composer to systematically guide construction of a sentence of text input. The natural language composer may launch with a plurality of preconfigured text input options, any of which can be entered, for example, by selecting the particular option. The text input options may include punctuation controls to simultaneously input the text option and appropriate punctuation to create a flowing, natural, and grammatically correct sentence. The plurality of punctuation controls provide a user flexibility to specify how the text sentence will appear. The configuration data and or a template may provide the preconfigured text input options, and may allow user customization of what preconfigured text input options are available.

The template editor component 310 (or simply "template editor") may be configured to enable a user to create a document template to guide creation of documents. The template editor 310 may allow a user to create a new template by adding (create) and mapping one or more categories of entries. A category may include a label, which can be used as a prompt in the navigator to indicate the type or category of an entry needed to create a document according to the template. In addition, sub-elements of each category can be added and mapped. A category may be considered a top level heading and a sub-element may define sub-headings under categories. Sub-elements can have an unlimited number of sub-elements. Accordingly, categories and sub-elements may define a simple tree structure with categories as the top level of the tree. Categories can have pertinent findings (positive or negative findings) which may populate a composer window when a user selects the type input control associated with the category. In contrast to sub-elements, categories may not have a click input control, only a record input control and a type input control. Sub-elements can be found by expanding each category. Sub-elements have a click input control, a record input control, and a type input control.

Categories and sub-elements can be mapped according to group and grading, as in coding, for example. Or they can be mapped to any logical system that allows each category or sub-element to be identified by a secondary permanent label, allowing the category or sub-element label to be handled as merely a label. The mapping may be considered an alias for the category or sub-element.

The sub-elements of a template provide additional options and or structure for composing an entry for a given category. The sub-elements may include findings. The findings defined in a template may specify auto-inserted data for a given category and/or sub-element. The auto-inserted data may include findings (a.k.a., pertinent findings), which may be either negative or positive. Findings can be added to the category or sub-element through the template editor. Findings are accessed by selecting the type input control and they exist in the top window of the composer. They may be personalized to each user's thought process to reduce the amount of typing and dictating that is necessary, by creating pre-defined entries that can be clicked on in the composer.

As can be appreciated, the template editor 310 may further enable editing, cloning, renaming, removing, etc. of templates. As previously mentioned, template creation components, such as for example the template editor 310, may be separate from the data input components of the input subsystem 120. For example, the template editor may be accessed via different interfaces and/or paths and/or may require different access permissions. Alternatively, the template editor 310 may be integrated with other components of the input subsystem 120, such that, for example, the template editor 310 can be accessed via the same paths and/or with the same permissions as, for example the navigator, the viewer, and/or the composer and a template could be created or modified concurrently with data input.

Figure 3B:
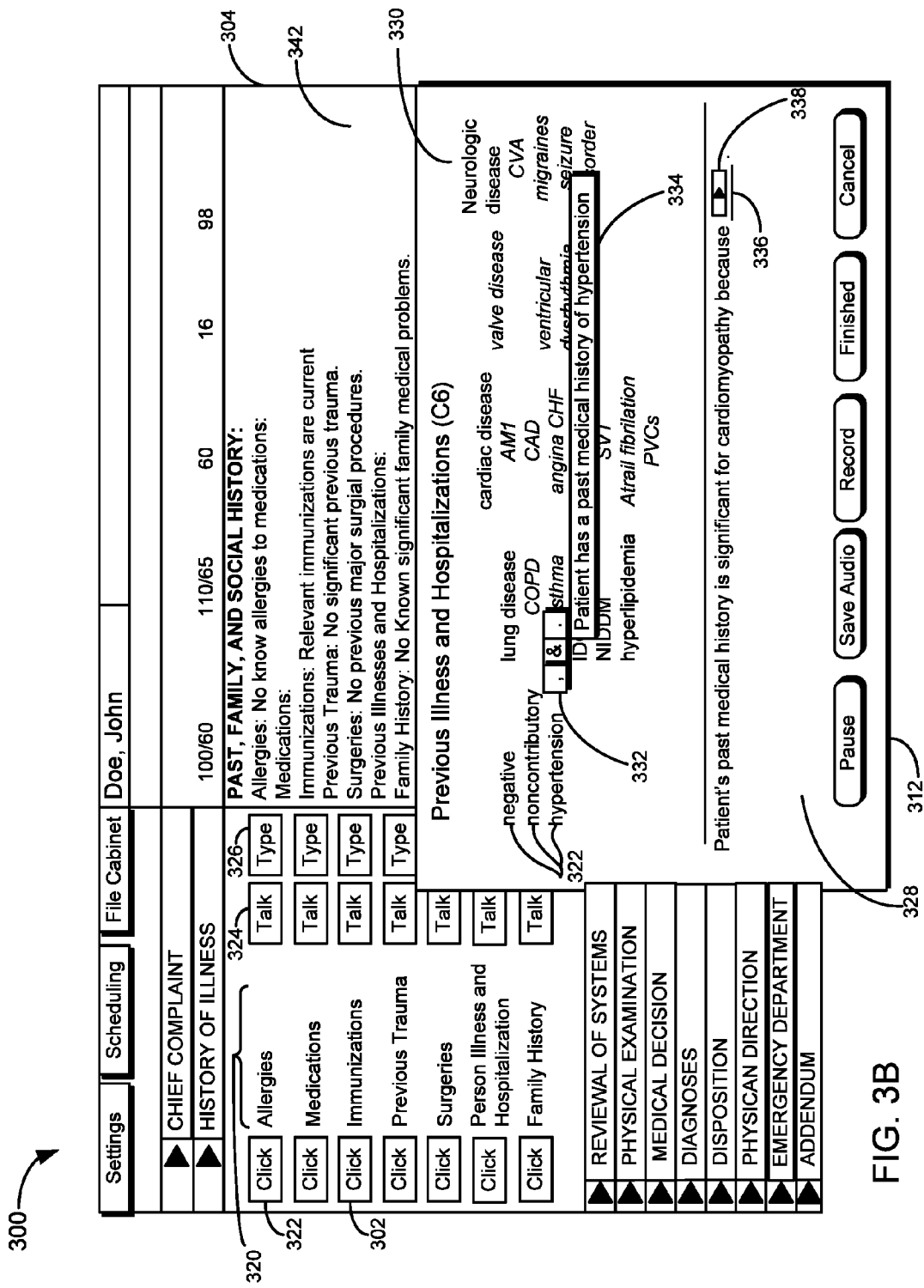
FIG. 3B illustrates a graphical user interface of an input subsystem of a document creation and management system, according to one embodiment of the present disclosure.

FIG. 3B illustrates one embodiment of a graphical user interface (GUI) 300 of an input subsystem 120 of a document creation and management system. The GUI 300 may present one or more of the various components of the input subsystem 120. In the illustrated embodiment, the GUI 300 provides a navigator 302, a viewer 304, and a composer 312.

The navigator 302 may include one or more prompts 320 to guide a user in the input to be entered to generate the content of a document. The prompts 320 indicate categories and/or sub-elements of categories of input to be gathered to generate a document. The prompts 320 may be configured to guide or substantially mirror a user's thought process of document creation (at least the user's thought process with regard to creation of a particular type of document; e.g., a medical record). In one embodiment, the prompts 320 may be configured to be customized and/or personalized to a particular user, and substantially mirror that particular user's thought process. A prompt 320 may be a label, a key word, a phrase, or the like to indicate information or other data to be input to generate the document. The prompts 320 may correspond to categories and/or sub-elements of categories specified by configuration data. In one embodiment the prompts 320 may correspond to categories and/or sub-elements of categories specified in a template and generated and customizable via the template editor, as described below with reference to FIG. 3C.

The navigator 302 may further include one or more input controls. The input controls may correspond to the prompts, such that activation or manipulation of an input control facilitates input of data that will be correlated to the corresponding prompt 320. In the illustrated embodiment, the navigator 302 presents a plurality of input controls for each prompt. A click input control 322 may be provided as a button. The click input control 322 may activate the auto-insertion component 306 (FIG. 3A) to automatically insert preconfigured data to compose into an entry relating to the associated category or sub-element of a category. A talk input control 324 (i.e., a record input control) may also be provided as a button. The talk input control 324 may activate the recorder 308 to record data and compose an entry relating to the associated category or sub-element of a category. A type input control 326 may also be provided in the navigator 302 as a button. The type input control 326 may launch the composer 312 enabling a user to input typed text and compose that text into an entry relating to the associated category or sub-element of a category.

The composer 312 may be launched as a pop-up window, as shown in the illustrated embodiment. The composer may provide a text box 328 to allow a user to type text input. The composer 312 may also provide a natural language composer 330, to guide construction of a structurally and grammatically correct sentence. The natural language composer 330 may provide a series of click input controls 322 corresponding to a plurality of preconfigured text input options 334, any of which can be entered, for example, by selecting a corresponding click input control 322 for the particular option. In the illustrated embodiment, the click input controls 322 are clickable labels (or links) providing a key word or abbreviation of the preconfigured text input options 334. When a user hovers over a click input control 322, the text of the corresponding preconfigured text input option 334 appears. The click input controls 322 of the composer, when clicked, insert the indicated text. The inserted text appears in the text box 328.

The text input options 334 may further be associated with punctuation click input controls 332 to present punctuation options associated with the preconfigured text input options. In the illustrated embodiment, the punctuation click input controls 332 appear when a user hovers over a text input option 334 (which in the illustrated embodiment are also click input controls). The punctuation click input controls 332 may allow simultaneous input of the text option and appropriate punctuation to create a flowing, natural, and grammatically correct sentence. The plurality of punctuation controls provide a user flexibility to specify how the text sentence will appear. The configuration data and or a template may provide the preconfigured text input options, and may allow user customization of the preconfigured text input options and punctuation click input controls. A history button may be provided in the composer to access previous document history, as described below.

The preconfigured text input options 334 may include one or more blanks 336, or areas that the user is required to fill in to complete the entry. To fill in a blank 336, the user may provide typed text by clicking on the blank 336 and typing. A use may also be enabled to tab to each of a series of blanks, and the composer may automatically move to and highlight the next available blank. A user may also be able to fill in a blank with recorded input by clicking a record input control 324 in the composer 330. Thus, a user can click, talk, or type to enter input via the composer 312. The user can simply click on, or tab to, the blank 336, and then click on the record input control 324 to activate the recorder 308 and provide dictation. The recorder 308 will record the dictation and create a dictation snippet. When a blank 336 is filled by a dictation snippet or other recorded input, the composer may display an icon 338 or other indication in the blank 336 to show that the blank contains recorded input. In the illustrated embodiment, the indication is a "play" icon 338, indicating that the user can click the play button to activate the recorder and playback the recorded input. During processing, this recorded input may be transcribed. If the transcription is available, the composer 312 may provide the text in the blank with or in place of the icon.

The viewer 304 may display an output document 342 to a user. The viewer presents the document currently being generated substantially as it would appear as if printed on paper. In other words, "what you see is what you get" (WYSIWIG). All of the individual entries of the document (collectively the content of the document) is displayed in the viewer with the formatting of the document. Additionally, if the individual entries have any associated formatting rules, those entries are presented according to the associated formatting.

The GUI 300 of the input subsystem 120 may also provide other features, such as a file cabinet interface, which allows a user to select previously generated documents to edit and/or complete. The GUI 300 may also provide a "Settings" tab, which may allow the user to access the template editor 310.

Figure 3C:
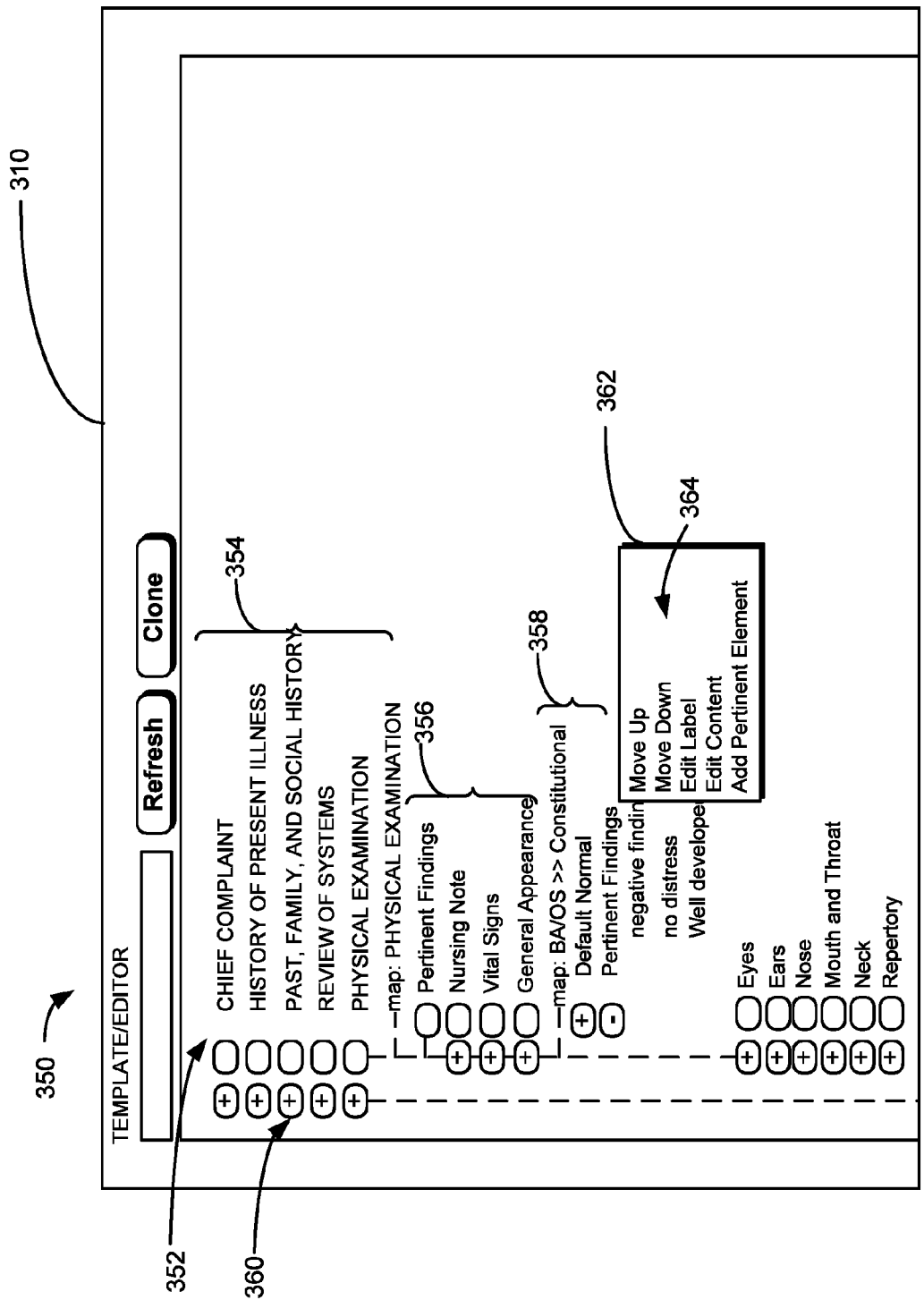
FIG. 3C illustrates another graphical user interface of an input subsystem of a document creation and management system, according to one embodiment of the present disclosure.

FIG. 3C illustrates another GUI 350 of an input subsystem of a document creation and management system, according to one embodiment of the present disclosure. The GUI 350 may comprise the template editor 310. The template editor 310 may allow a user to create and/or modify templates of documents. A template may specify categories of content of a document and also the sub-elements of those categories. Furthermore, a template may specify any preconfigured text for any of the categories and/or sub elements. The template may further specify formatting rules for a document as a whole, or for an individual category or even individual sub-elements. These features of a template may be configurable via the template editor 310.

The template editor 310 may present a list of categories 354, and category sub-elements 356, and even sub-elements of the sub-elements 358, and so on. The categories 354 and sub-elements 356, 358 may be presented as an expandable and collapsible tree structure 352. The tree structure gives the categories 354 and sub-elements 356, 358 an inherent ordering. Expansion controls 360 allow categories and/or sub-elements to be expanded or collapsed for convenient viewing of the tree structure 352. The tree structure 352 may be analogous to an outline of a document to be created. Changing the ordering of the categories 354 and sub-elements 356, 358 may change the structure of the content of a document. The navigator 302 may use the tree structure 352 to generate its prompts to guide user input to generate the entries (i.e., the content) of a document. The composer 312 may also use this tree structure to generate preconfigured input options.

The template editor 310 may also allow a user to define or modify the structure of categories 354 and sub-elements 356, 358. For example, right clicking on a category may present a list 362 of actions 364, including "Move Up," "Move Down", "Edit Label," "Edit Content," and/or "Add Pertinent Element." The "Move Up" and "Move Down" actions modify the position of a category 354 and/or sub-element 356, 358 in the tree structure. The "Edit Label" action may allow a user to specify a label for a category 354. The label may be used by the navigator 302 and the composer 312 as a prompt 320 (see FIG. 3B). The "Edit Content" action may allow a user to specify preconfigured data to be inserted into an entry in response to activation of a click input control. The preconfigured data may be any type of data, including but not limited to text, image data, audio data, and video data. The pre-configured data may include preconfigured text input options 334 (see FIG. 3B) to be presented in a natural language composer 330. A user may also be able to specify blanks 336 requiring additional user input via type or record. The "Add Pertinent Element" action may allow a user to add new categories and sub-elements, or to map an element to a defined mapping. A mapping enables one or more categories to be mapped (or grouped) together. The mapping may allow, for example, a sub-element "Skin" to be associated with a sub-element "Epidermis." Accordingly, one template may use the Skin sub-element, while a second template may use the Epidermis sub-element, and data for either element is recognized by the system and related to the same mapping.

The template editor 310 may allow a user to create multiple and templates, so as to have a number of different templates available for various types of documents. The template editor 310 may also allow the user to modify and to manage the various templates. The template editor 310 may also allow a user to clone an existing template, which could then be quickly and easily customized to generate a new template for a different type of document.

Figure 4:
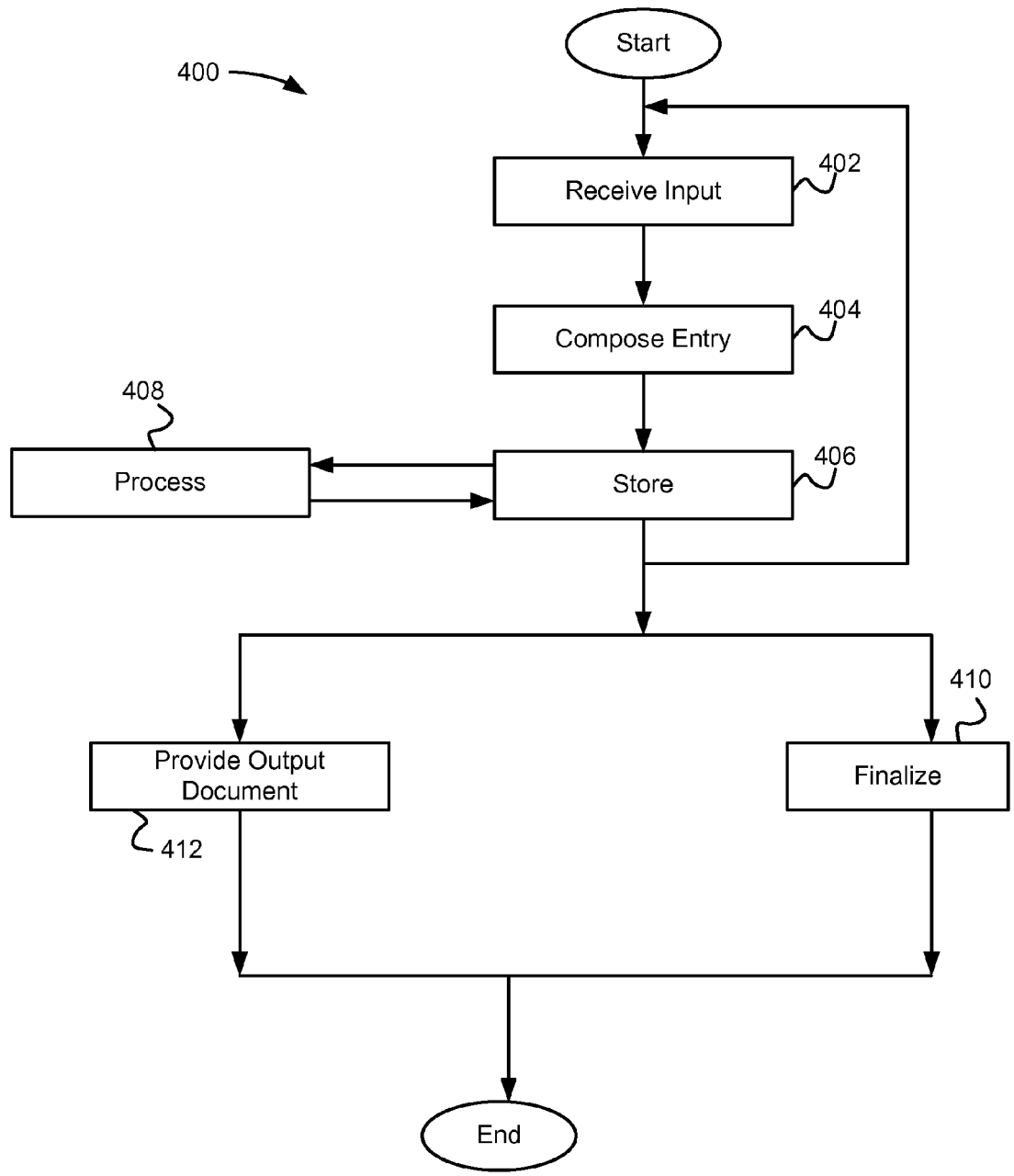
FIG. 4 illustrates a high-level flow diagram of a method for document creation and management, according to one embodiment of the present disclosure.

FIG. 4 illustrates a high-level flow diagram of one embodiment of a method for document creation and management 400. Input data is received 402, the input data is composed 404 into one or more entries to form the content of a document. The document, including both formatting rules and content (e.g., entries), is stored 406, including storing 406 each of the entries of the document as discrete elements. The document and/or one or more of the entries may be processed 408 and again stored 406. The document may be finalized 410, and/or an output document may be provided 412 by presenting the content (e.g., entries) of the document according to the formatting rules of the document.

In one implementation of the method 400, a document creation and management system may be configured to receive 402 input data. Data may be suitably input via any interface, mechanism, module, and/or means, now known or later developed. For example, data may be input via the input subsystem 120 shown in FIG. 1A and described in greater detail with reference to FIGS. 3A and 3B. Moreover, data may be input by multiple users and/or sources, and may be input simultaneously in parallel and/or in a serial fashion. Additionally, data may be input at or from multiple locations, as desired. Once at least a portion of the data is input, the data may be suitably composed 404 as one or more entries of a document. As explained, an entry may comprise, but is not limited to, any of text, image data, audio data, and video data that can be entered into or used to create the contents of a document. Moreover, an entry may include one or more other entries or another document.

Composing 404 input data into entries allows the input data to be divided in any suitable manner and/or according to any suitable pattern, criteria, and/or template, as desired. For example, the data may be divided into portions input via typing, portions auto-inserted via clicking and/or touching, portions input via recording (e.g., talking/dictation), and so on. The entries may further divide input data according to predefined categories or subjects (e.g., based on physiological characteristics, such as relating to a body part, technical content, and or any desired classification). Additionally, composing 404 input data into entries enables input data to be divided based on time. For example, entries may be associated and/or sorted based on time, including date of input, minute of input, second of input, and so forth. In an additional example, composing 404 input data into entries allows input data to be divided based on one or more user actions, for example beginning data entry via a first method (e.g., recording), stopping data entry via a first method, beginning data entry via a second method, stopping data entry via a second method, and/or the like. In an exemplary embodiment, data input via talking is divided up into one or more dictation snippets (e.g., a portion of recorded human speech), each containing a portion of data input via talking.

When at least a portion of data has been received 402 and composed 404 into entries, the document creation and management system may be configured to group or otherwise associate the entries of a document together for storage as a document. The content of a document is stored 406 separate from the formatting rules of the document, thereby allowing the content to be formatted or otherwise arranged in any desirable manner. Moreover, the content of a document is stored 406 as discrete entries. The entries are stored 406 discretely and in association as a document. Storing 406 the entries discretely can enable improved data privacy and confidentiality, or otherwise enable compliance with data security requirements and privacy/confidentiality laws (e.g., HIPAA, HITECH). Storing 406 entries discretely may allow delivery of one or more entries to a processing subsystem entity (e.g., a transcription service, editing service) without attaching identifying demographic information, which provides a layer of security for both a user of the document creation and management system or method and the subject (e.g., patient) of the document. A processing subsystem 126 (see FIGS. 1B and 1C) can work on processing the entries without specific knowledge of the subject, assuming the document relates to a person. Storing 406 entries discretely as separate objects also can enable improved processing efficiency by allowing delivery of one or more entries to one or more separate processing entities or processing subsystems. Accordingly, entries can be processed in parallel, thereby enhancing efficiency of the method and/or system as a whole.

In one embodiment, the document may be stored 406 again upon composition of a new entry. Accordingly, a document, including its new discrete entries, is stored 406 at various points of creation of the document. The updated document may be stored as a new version of the document. Alternatively, the updated document may simply be stored anew in its updated state, effectively replacing an old version. In one embodiment, only the new entries are saved along with information indicating each new entry's association with other entries of a document, to integrate the new entry into the document.

A document creation and management system may be configured to process 408 a document, including processing one or more of the entries of a document. Processing 408 may include any form of preprocessing, filtering, editing and the like of input data as composed in an entry. The entries may be processed, or alternatively the input data contained in an entry may be processed. The input data may be processed via any suitable means and according to any suitable criteria, algorithms, and/or templates, as desired. The input data may be processed directly by the document creation and management system; alternatively, the document creation and management system may be configured to transmit, exchange, and/or otherwise deliver the input data to a separate processing subsystem 126 (see FIGS. 1B and 1C) for processing. Moreover, the document creation and management system may be configured to process certain kinds of input data (for example, data input by typing) directly, and may be configured to transmit certain other kinds of input data (for example, data input by talking) to a separate processing subsystem for processing.

The processing 408 may be performed via any suitable algorithms, rule sets, methodologies, and/or the like. The processing 408 may include conventional data processing techniques, for example, but not limited to, transcribing, annotating, encrypting, decrypting, spell checking, formatting, indenting, spacing, bolding, italicizing, underlining, merging, inserting, concatenating, cropping, searching, highlighting, marking up, and/or the like. Moreover, the processing 408 may be performed sequentially; however, the processing 408 may also be performed in a parallel and/or distributed manner. For example, a first entry of a document may be processed at the same time as a second entry of the document, a third entry of the document, and a fourth entry of the document, and so on, rather than each entry being processed sequentially. In this manner, the processing 408 of a document as a whole can be completed faster. Moreover, because each entry may contain data having different processing guidelines and/or requirements (for example, security and/or privacy guidelines), processing of each entry may be suitably customized, as desired, such as by routing processing of various entries to various processing subsystems 126.

The processing 408 may be performed within the document creation and management system; however, the processing 408 may also be performed at a location external to the document creation and management system. In accordance with various aspects, the processing 408 may include transmitting one or more dictation snippets to a transcription service provider for transcription. In order to accelerate the processing 408, an entry including a dictation snippet may be sent to a transcription service provider as soon it is created, instead of waiting for all dictation snippet entries to be composed. Moreover, based on a desired criteria, for example the contents of a dictation snippet (e.g., a dictation snippet containing personally identifiable information, protected medical information, and/or the like), entries including dictation snippets may be routed, grouped, transmitted, encrypted, secured, and/or otherwise processed in a manner configured to achieve a desired level of security, confidentiality, and/or privacy for the information contained in a dictation snippet. For example, a first entry containing a dictation snippet having a first desired privacy level may be sent to a first transcription service provider, and a second dictation snippet having a second desired privacy level may be sent to a second transcription service provider. In this manner, dictation snippets having different processing, security, and/or privacy requirements may be processed separately and thus more efficiently. Moreover, contextual information (e.g., information relating to at least one of complaint specificity, procedure, document type, and/or the like) may also be transmitted with a dictation snippet to a transcription service provider in order to facilitate efficient processing of the dictation snippet.

Output data resulting from processing may be received from one or more processing subsystems responsive to delivery of input data to the processing subsystems as previously discussed. For example, a transcription of a dictation snippet may be received from a processing subsystem responsive to delivery of the dictation snippet to the processing subsystem. Output data may be stored in any suitable location for retrieval and/or use by the document creation and management system.

Output data may be formatted in any suitable manner, as desired. For example, output data may comprise formatted text, embedded media (for example, audio, video, images, and/or the like), flags, check boxes, macros, highlights, underlines, and/or the like, or combinations of the same. Moreover, output data may be encrypted, protected, and/or otherwise configured with restricted access and/or availability in order to allow output data to be viewed and/or used only by an authorized user.

Once at least an entry, or data contained therein, has been processed 408, the document may be stored 406 again. A preliminary document (a document that has not been finalized) can be modified by opening the document for editing and again receiving input 402. A document can also be finalized 410. A finalized document, according to one embodiment cannot be modified, edited, altered, or the like in any way. In the context of medical records, the document becomes a permanent record. Providing entering additional data relating to a finalized record may require creation of a new document as an addendum. The new document may include the finalized document as an entry, but the finalized document remains unchanged and unalterable. The additional information could be added as new entries to the new document.

At any time, a stored document may be provided 412 as an output document. As previously explained, an output document is a form of a document in which the content of a document is presented according to the associated formatting rules. An output document is analogous to a presentation of a document. An output document may be presented in any suitable format, including paper or electronic formats, and may be preliminary or finalized. For example, a viewer 304 may provide an output document in a GUI 300 (see FIG. 3B) of an input subsystem 120 (see FIGS. 1A and 3A). After finalizing 410 a document or providing 412 an output document the method 400 may end.

Figure 5:
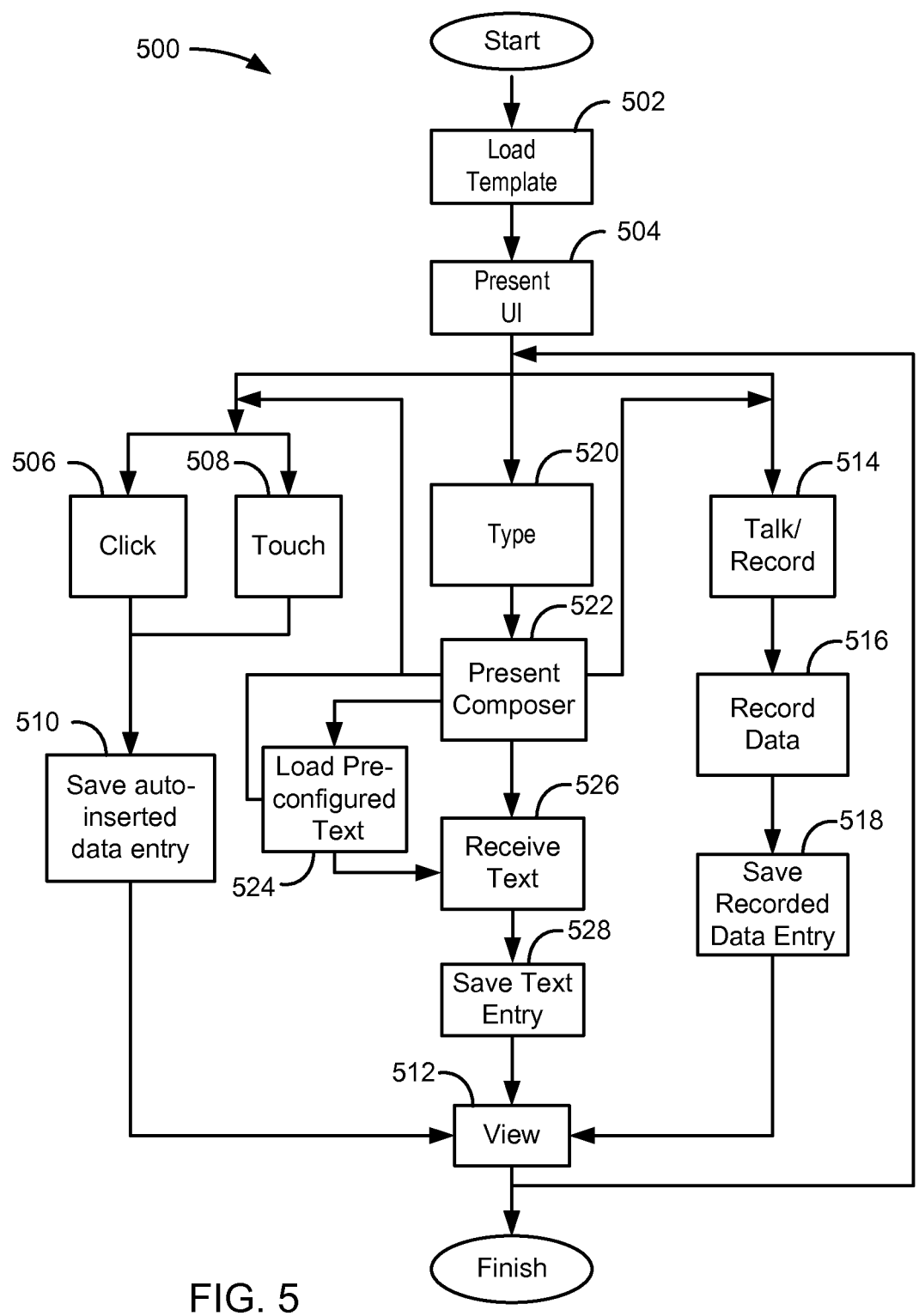
FIG. 5 illustrates a flow diagram of a method of receiving input and composing entries via an input subsystem of a document creation and management system, according to one embodiment of the present disclosure.

FIG. 5 illustrates a flow diagram of a method 500 of receiving input and composing entries via an input subsystem of a document creation and management system, according to one embodiment of the present disclosure. A template may be loaded 502 to provide document arrangement, structure, and/or formatting rules for the document being generated. A user interface, such as GUI 300 (FIG. 3B) may be presented 504. From the user interface, the method may proceed a number of different ways, depending on a user's selected manner of providing input data.

An activation of a click input control 506 may be received, or an activation of a touch input control 508 may be received, and auto inserted pre-configured data may be composed into an entry and saved 510. The entry may then be viewed 512, for example in the context of an output document in a viewer 304 of the GUI 300 (see FIG. 3B).

Alternatively, an activation of a talk (or record) input control 514 may be received. Input data is recorded 516 and an entry is composed and saved 518 containing the recorded data. Again, the entry may then be viewed 512. Prior to processing, the entry containing non-visual recorded input may be displayed as an icon or other indication of non-visual recorded data.

Alternatively, an activation of a type input control 520 may be received, and the composer may be presented 522. The composer may allow activation of a click input control 506 to auto-insert preconfigured data. The composer may also allow activation of a talk (or record) input control 514 to record data. The composer may also optionally load 524 any preconfigured text. Type text is received 526 and an entry is composed and saved 528 containing the typed text. Again the entry may then be viewed. The method 500 may then substantially repeat with activation of another input control or may simply end.

Figure 6:
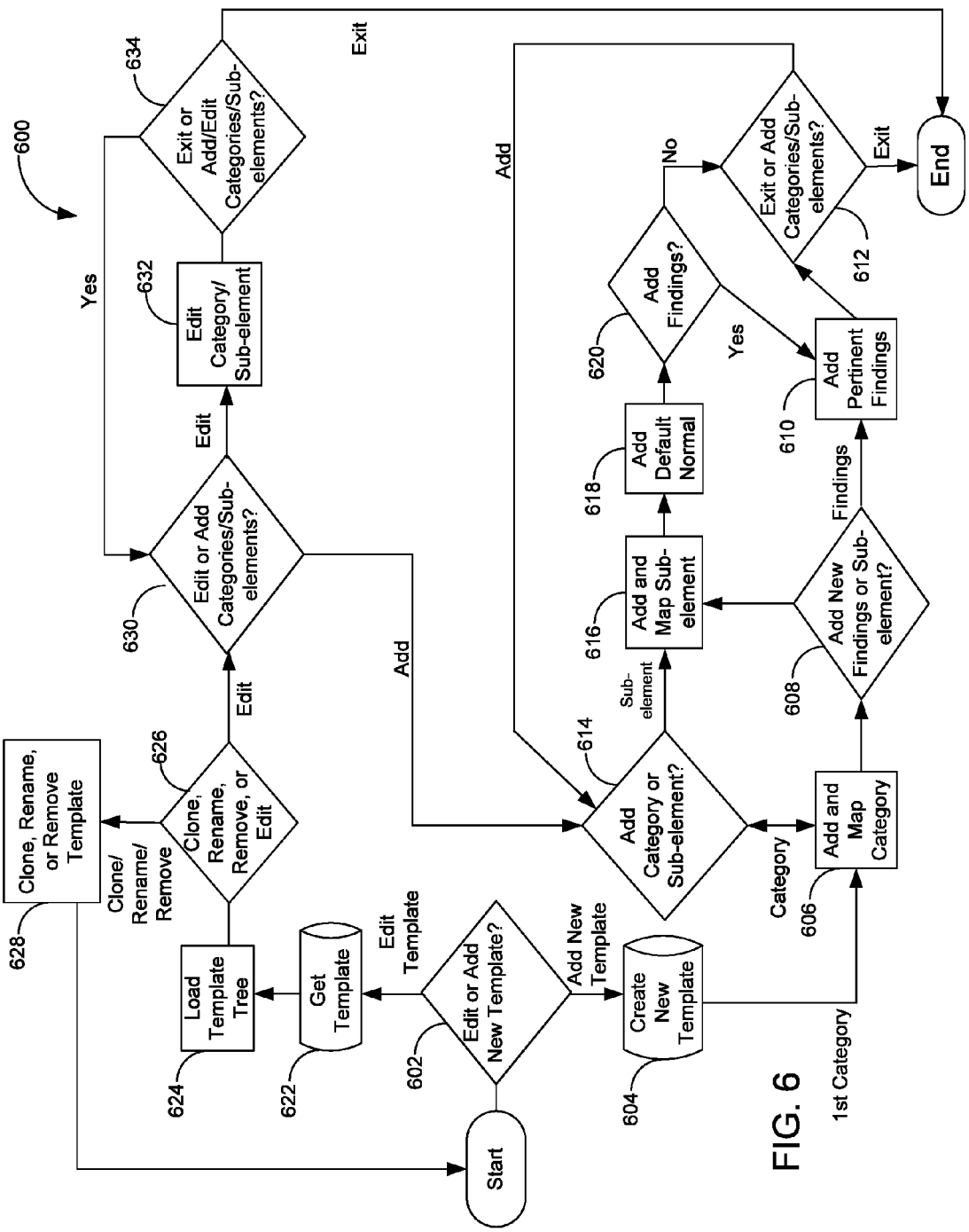
FIG. 6 illustrates a flow diagram of a method of template creation and editing via an input subsystem of a document creation and management, according to one embodiment of the present disclosure.

FIG. 6 illustrates a flow diagram of method 600 of template creation and editing via an input subsystem of a document creation and management. A decision 602 is made whether to edit an existing template or add a new template. If the decision 602 is made to add a new template, then a new template is created 604. Creating 604 a new template may comprise loading a system default template without any categories or sub-elements. A new category can be added 606 and mapped. A decision 608 is made to add new findings or add a new sub-element. If the decision 608 is made to add new findings, then the pertinent findings may be added 610. The pertinent findings may include, for example, preconfigured input data. Another decision 612 is made whether to exit or add a new category (or sub-element). If the decision 612 is made to add a new category (or sub-element), then another decision 614 is made whether to add a category or a sub-element. If the decision 614 is made to add a category, then the method 600 adds a category and proceeds as has been described. If the decision 614 is made to add a sub-element, then a sub-element is added and mapped 616. A default normal is added 618 to the new sub-element. A decision 620 is made whether to add findings, which can be added 610 as was described. If no findings are added 620, then again a decision 612 is made whether to exit or add categories or sub-elements.

If the decision 602 is made to edit an existing template, then the template is obtained 622 and the template tree of the template is loaded 624. Another decision 626 is made whether to clone, rename or remove the template or to edit the template. If the decision 626 is made to clone, rename, or remove the template, then the template can be cloned, renamed or removed 628 and the method can repeat. If the decision 626 is made to edit the template, then another decision 630 is made whether to edit categories (or sub-elements) or add categories (or sub-elements) to the template. A decision 630 made to add categories (or sub-elements) may result in the method 600 proceeding, as previously described for adding categories or sub-elements, to decision 614. If the decision 630 is made to edit categories (or sub-elements) then a category or sub-element can be selected and edited 632. Editing may be done as described by changing the label and/or the content of a category or sub-element, by altering formatting, or the like. A decision 634 is made whether to exit or to further modify the template being edited. If the decision 634 is made to continue to modify, the method 600 proceds again toe decision 630 whether to edit a category (or sub-element) or to add a category or sub-element.

Figure 7A:
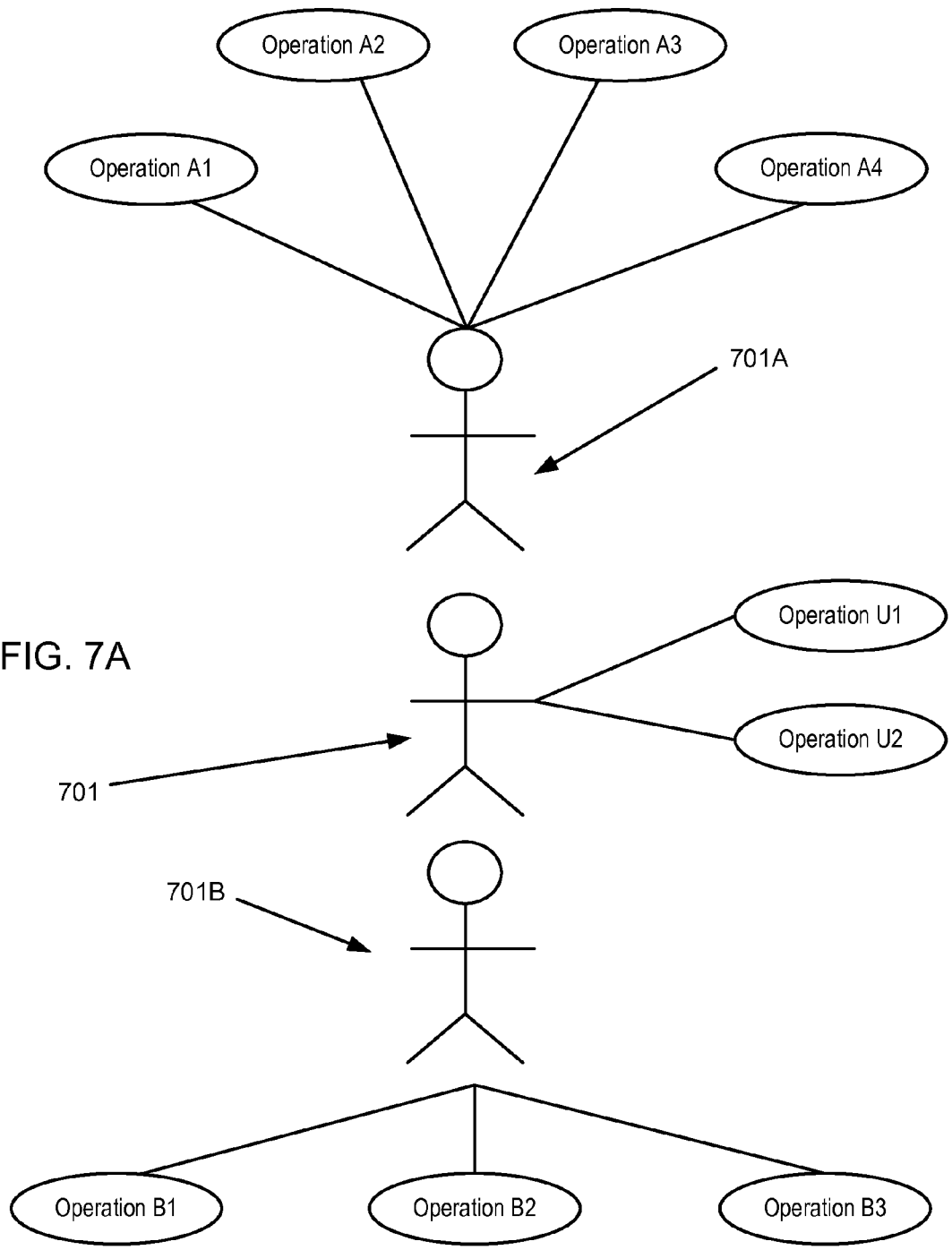
FIG. 7A illustrates use cases for a document creation and management system, according to one embodiment of the present disclosure.

FIG. 7A illustrates use cases for a document creation and management system. In one embodiment, a user 701 may be permitted to conduct certain operations, for example general operations U1 and U2, via a document creation and management system 100 (see FIG. 1A). A particular subtype of user 701, for example user 701A, may be permitted to conduct operations A1 through A4 in addition to operations U1 and U2. A different user subtype, for example user 701B, may be permitted to conduct operations B1 through B3 in addition to operations U1 and U2. Moreover, each operation may be restricted to accessing particular information and/or data within the system 100. In this manner, certain operations and/or data may be restricted to a particular user and/or class of users, as desired. Moreover, additional users may be permitted to conduct operations associated with multiple user subtypes. For example, a particular user 701C (not shown) may be permitted to conduct operations A1 through A4 as well as operations B1 through B3. In this manner, restricted access, administrative control and/or hierarchical control of information within the system 100 is facilitated. Moreover, any suitable access restrictions, levels, groups, and/or the like may suitably be provided in order to facilitate data security and/or efficient utilization of the system 100.

Figure 7B:
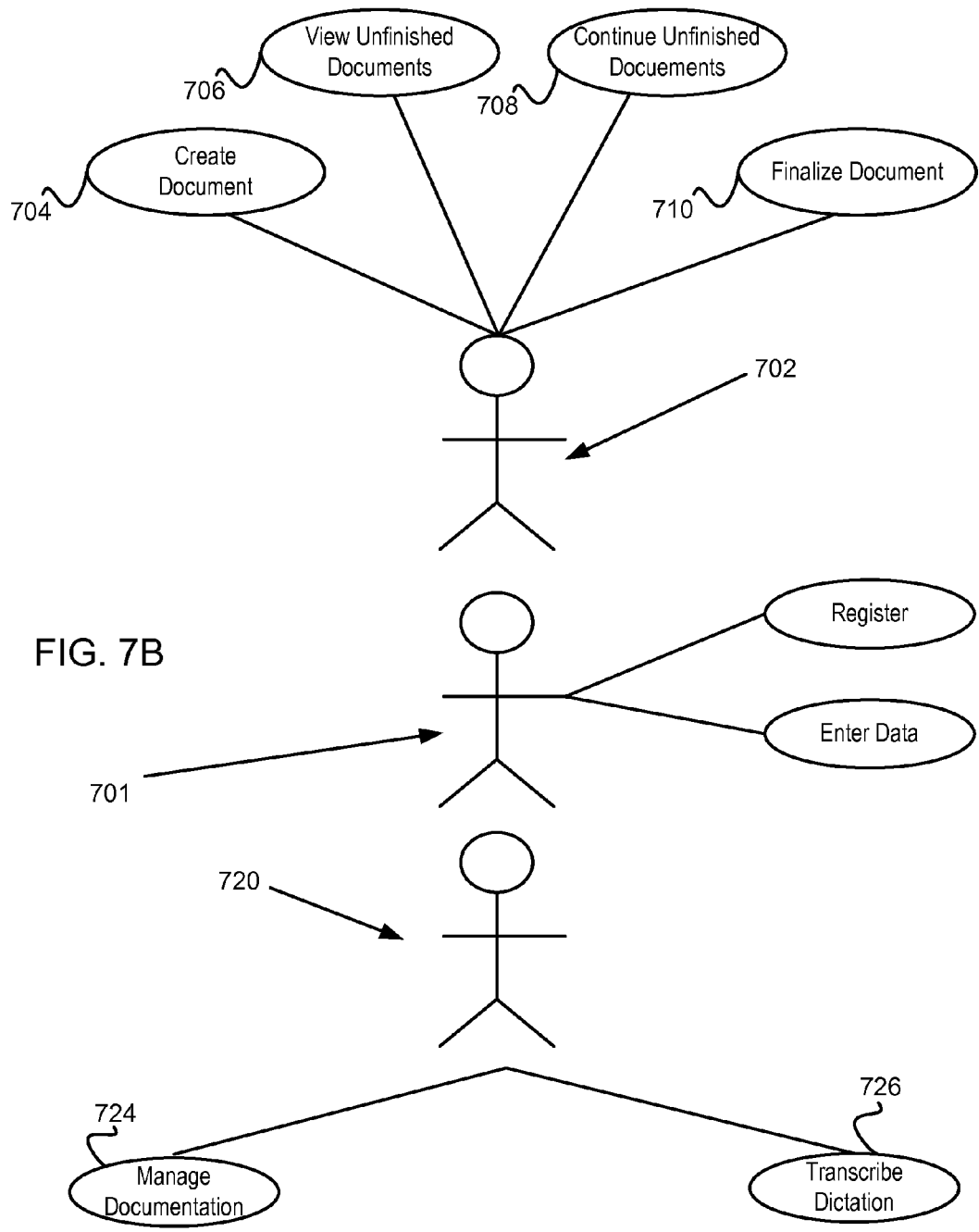
FIG. 7B illustrates use cases for a document creation and management system to create and manage medical records, according to one embodiment of the present disclosure.

As a more specific example of one embodiment, turning now to FIG. 7B, a user, for example a physician 702, may be able to create new documents 704, view unfinished (or preliminary) documents 706, continue an unfinished (or preliminary) document 708, finalize a document 710, and so forth. Another user, for example a staff member 720, may be able manage patient documents 724 and transcribe dictation 726, and so forth. Moreover, the system 100 may also be configured to facilitate, implement, and/or support any suitable operation desired by a user, for example a physician. In one embodiment, the system may be configured to facilitate a physician 702 creating and/or editing a document.

Figure 8:
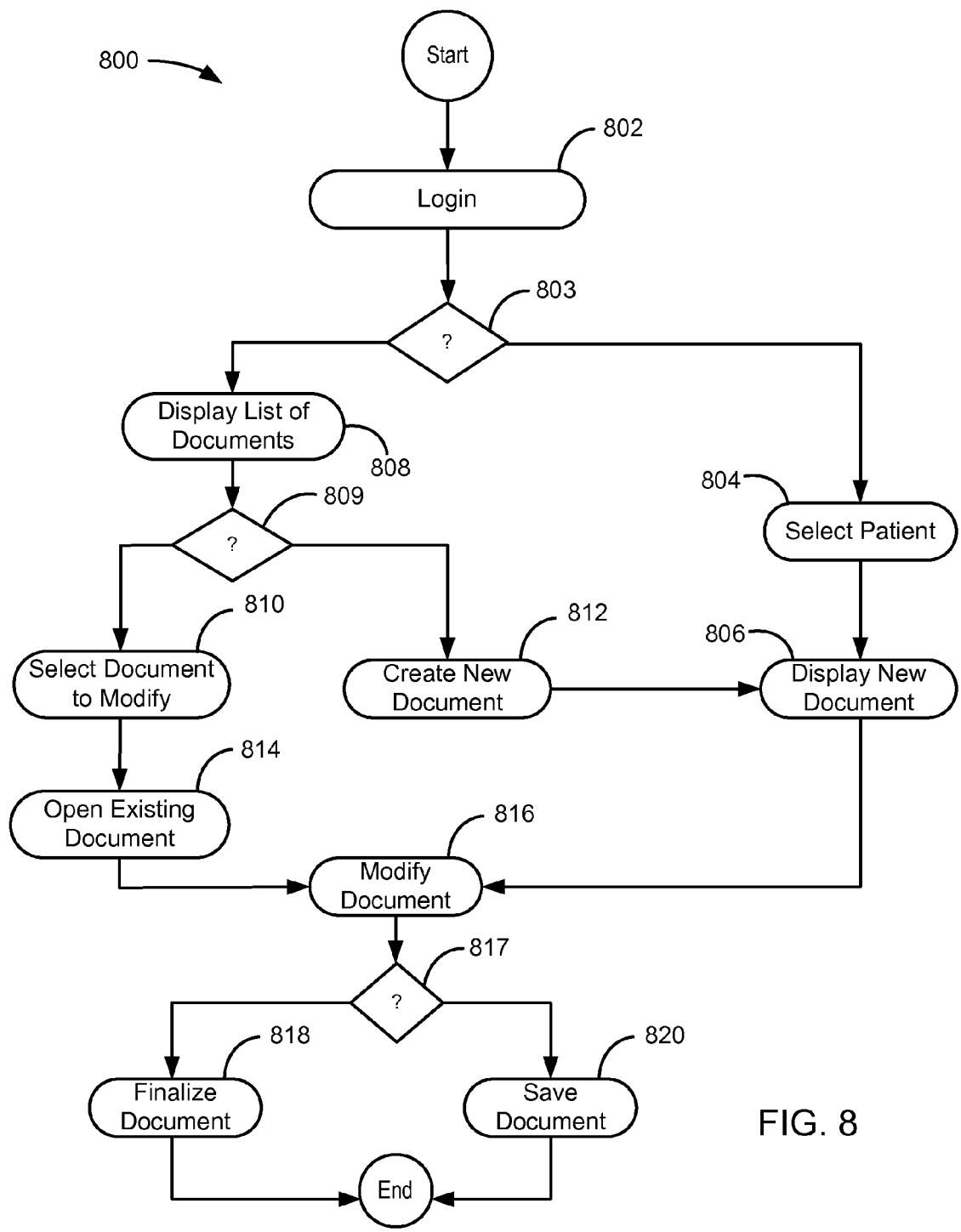
FIG. 8 illustrates work flow within a document creation and management system, according to one embodiment of the present disclosure.

FIG. 8 illustrates a work flow 800 within one embodiment of a document creation and management system. A user may login 802 to a document creation and management system. The user may then determine 803 whether to create a new document associated with a patient or select from a list of preliminary (i.e., not finalized) documents to complete. The user may select 804 a patient from a list and create 806 a new document associated with the patient. The document may be created via use of any suitable input and/or information management methodologies and/or techniques, including the techniques described above. Alternatively, a list of preliminary documents may be displayed 808 and the user can browse that list and determine 809 whether to select 810 one of the preliminary documents to modify or elect to create 812 a new document. If an existing document is selected 810 for editing, the document may be opened 814 and may be modified 816 as desired. Moreover, if a new document is opened 814, the document may also be modified 816. After edits are made, a determination 817 may be made to finalize 818 the document or save 820 the document for further editing. A user may create, edit, and/or revise documents in any order and/or via any suitable interface or functionality provided by a document creation and management system.

Figure 9:
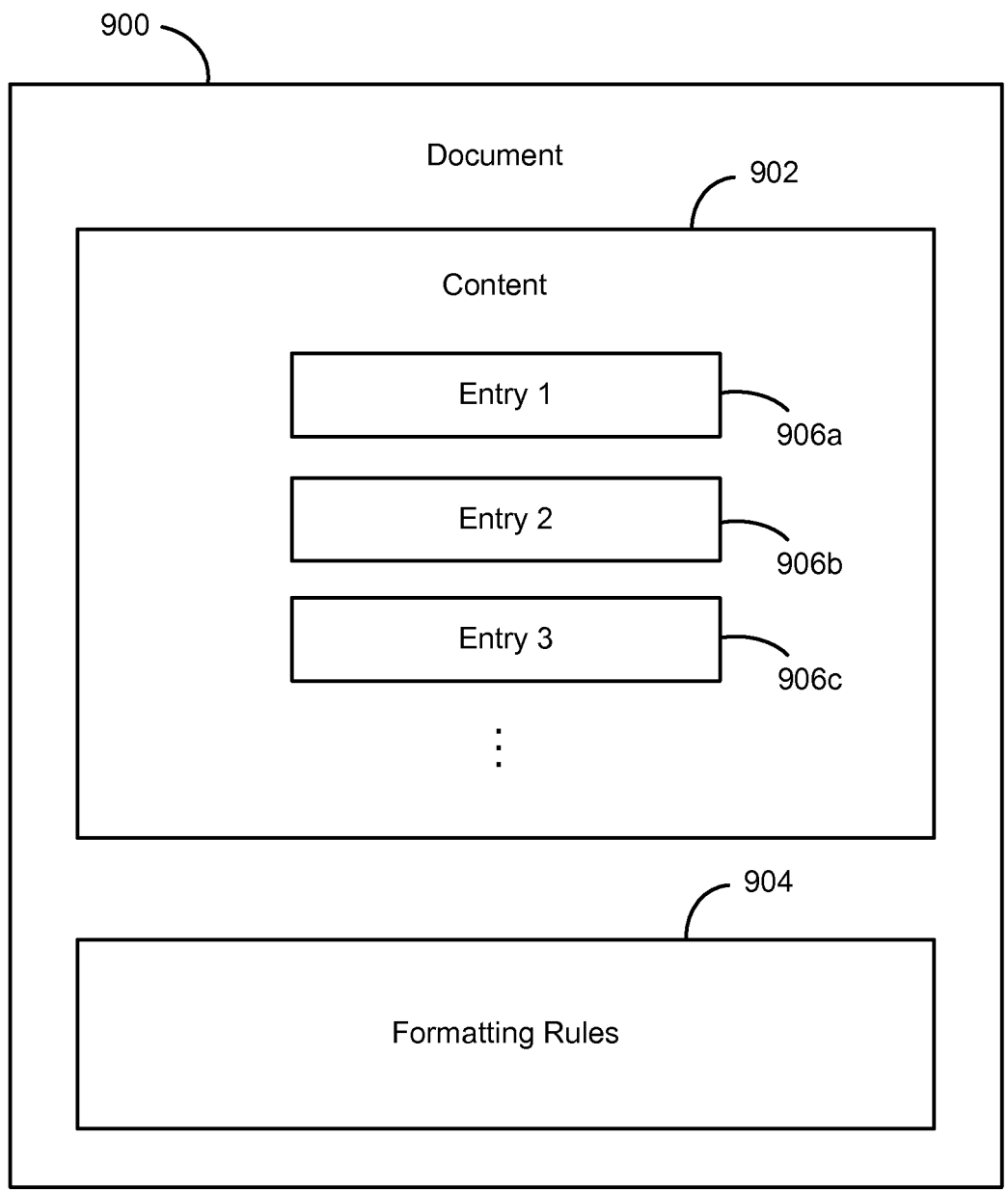
FIG. 9 illustrates a block diagram of a document, according to one embodiment of the present disclosure.

FIG. 9 illustrates a block diagram of one embodiment of a document 900, according the present disclosure. The diagram illustrates that a document 900 includes content 902 and formatting rules 904. The document 900 may further include other components, which are not illustrated in FIG. 9, including for example headers, footers, security features (e.g., permissions, digital rights management, etc.), routing rules for processing, encryption, document status information (e.g., preliminary, finalized), and the like. The content 902 of the document 900 may be stored as individual, discretely stored entries 906a, 906b, 906c in association. In one embodiment, the document 900 may be stored in a relational database as an element of a table providing information associating various document entries 906a, 906b, 906c. The association information of the document may then refer to the individual document entries 906a, 906b, 906c stored separately and discretely.

As mentioned previously, storing the entries discretely can enable improved data privacy and confidentiality, or otherwise enable compliance with data security requirements and privacy/confidentiality laws (e.g., HIPAA, HITECH). Storing entries discretely may allow delivery of one or more entries to a processing subsystem entity (e.g., a transcription service, editing service) without attaching identifying demographic information, which provides a layer of security for both a user of the document creation and management system or method and the subject (e.g., a patient) of the document. Entries can be processed individually and without any information about a subject (e.g., a patient) of the document, assuming the document relates to a person. Storing entries discretely as separate objects also can enable improved processing efficiency by allowing delivery of one or more entries to one or more separate processing entities. Accordingly, entries can be processed in parallel, thereby enhancing efficiency of the method and/or system as a whole.

FIG. 10 illustrates an output document 1000 of a document (e.g., a patient interaction record) generated by a document creation and management system, according to one embodiment. The output document 1000 may be generated by providing input data according to a document template. The input data may be stored as entries. The output document 1000 presents the entries of a document according to the formatting rules of the document and/or entries. As can be appreciated, other formats, configurations, record types, and/or the like, and not only patient interaction reports and/or other medical records, are considered to be within the scope of the present disclosure.

Figure 11:
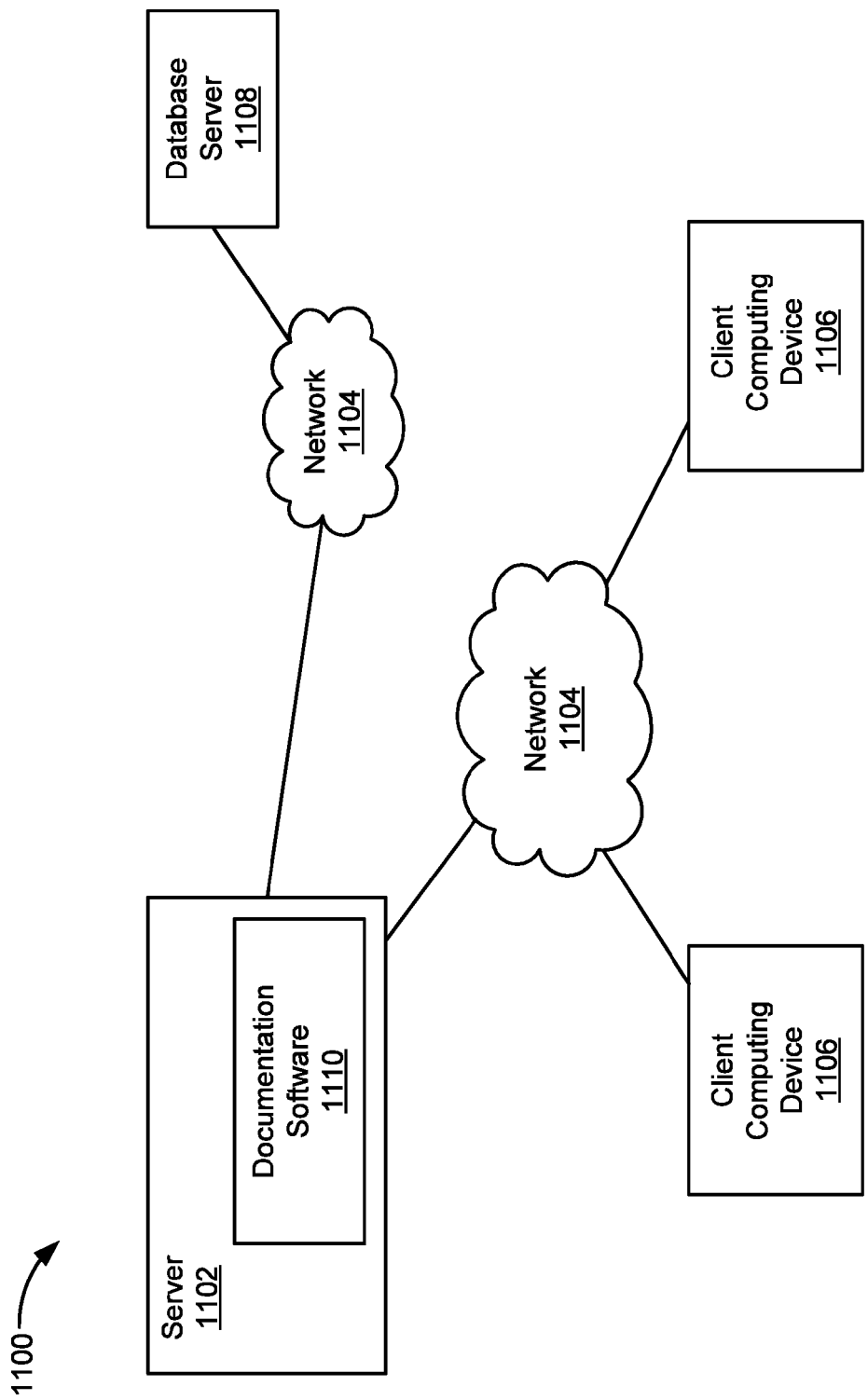
FIG. 11 illustrates a block diagram of a document creation and management system deployed in a client-server model, according to another embodiment of the present disclosure.

FIG. 11 illustrates a block diagram of yet another embodiment of a document creation and management system 1100, deployed as a client-server model. The system 1100 may comprise a server 1102, a network 1104, one or more client computing devices 1106, and a database server 1108. Further, one or more of the system components, including but not limited to a input subsystem 120, a document creation subsystem 122, a processing subsystem 126, and a data port subsystem 130, as explained with reference to FIGS. 1A-1C, may be embodied on the server 1102 as document creation software 1110. A document storage subsystem 124 and configuration data 128, as described with reference to FIGS. 1A-1C, may be embodied on the database server 1108.

The server 1102 may be any computing device configured to process (e.g., store, retrieve, modify, and/or the like) data. In various exemplary embodiments, the server 1102 comprises various processors (e.g., x86 instruction set based processors, SPARC processors, PowerPC processors, reduced instruction set computing (RISC) processors, and/or the like), communication interfaces (e.g., transmission control protocol/internet protocol (TCP/IP) interfaces, Ethernet interfaces, wired interfaces, wireless interfaces, and/or the like), data storage components (e.g., disk drives, memory, and/or the like), and/or software (e.g., operating systems, application software, and/or the like). Server 1102 may be configured to communicate with the one or more client computing devices 1106. For example, the input subsystem 120 (FIGS. 1A-C) of the document creation software 1110 may be deployed as a web application, such that a user interface of the input subsystem 120 is served to the one or more client computing devices 1106 as a web page and input provided to the web page is communicated back to the server 1102.

The one or more client computing devices 1106 may be any computing device configured for interaction with a user. In one embodiment, a client computing device 1106 may comprise a personal computer with a general-purpose operating system (for example, Microsoft Windows) operative thereon. However, a client computing device 1106 may comprise any server, desktop computer, laptop, netbook, smartphone, thin client, and/or the like, suitable for allowing interaction with the network 1104, the server 1102, and/or the document creation software 1110. The client computing device 1106 may comprise a browser to present a web interface served from the server 1102 and to enable user input.

The various parts of the document creation and management system 1100 may be communicatively coupled via any suitable means, for example via an electronic communication network 1104. The network 1104 may comprise multiple sub-networks, computers, servers, routers, and/or the like, as known in the art. In one embodiment, the network 1104 is a TCP/IP network (e.g., the Internet). Moreover, the network 1104 may comprise any suitable components configured to allow communication between the client computing device 1106, the server 1102, the database server 1108, and/or the like. The network 1104 is illustrated in FIG. 11 as two separate clouds to illustrate, for example, that in one embodiment the database server 1108 may be coupled to the server 1102 via a local and/or private or secure network, while the client computing devices 1106 may be coupled to the server 1102 via a different network, such as for example, the Internet.

The database server 1108 may comprise any suitable combination of hardware and/or software configured to allow storage, retrieval, and/or operations on data. The database server may include one or more databases, such as for example a relational database, a hierarchical database, a distributed database, and/or the like and/or combinations of the same, as desired. The database server 1108 may also be configured to encrypt, secure, and/or otherwise protect and/or restrict access to data. The database server 1108 may be communicatively coupled to the server 1102 and/or to the client computing device 1106. The database server 1108 may be configured to receive data from the document creation software 1110, and may be further configured to retrieve and/or process data responsive to requests from the document creation software 1110. For example, the database server may be configured to receive a document, including the document entries, and store the document by storing the entries discretely and in association with one another.

The document creation and management system 1100 may also suitably interface with any number and/or type of external systems, for example systems configured for data processing. Because document entries are stored separately and discretely, processing of entries can be flexible and involve any number of internal and/or external processing subsystems 126 (see FIGS. 1B-C). For example, the document creation and management system 1100 may be configured to enable parallel data processing, by routing a first entry to a first processing subsystem system and routing a second entry to a second processing subsystem. In another example, a document creation and management system 1100 may be configured to route processing of sensitive and/or private data separately from processing of non-sensitive and/or public data.

As will be appreciated, in another embodiment, the document creation software 1110 may be operable on one or more of the client computing devices 1106. For example, the input subsystem 120 (see FIGS. 1A-C) may be operative on the client computing devices 1106 and provide composed entries to the document creation subsystem on operating on the server 1102.

The document creation software 1110 may comprise any appropriate software components, programs, or group of programs (e.g., the document creation software 1110 may comprise various processes, threads, modules, daemons, and/or the like) operative on one or more of the client computing devices 1106 and/or the server 1102. The document creation software 1110 may be configured to enable operations on information associated with a patient, including for example entry, editing, storage, retrieval, processing, transmission, printing, transcription, encryption, decryption, and/or the like. The document creation software 1110 may comprise any suitable algorithms, routines, modules, interfaces, components, and/or the like. Moreover, the document creation software 1110 may be configured to operate on multiple processors and/or across multiple client computing devices 1106 and/or servers 1102 in a distributed manner. Further, multiple instances of the document creation software 1110 may be simultaneously operative. For example, the document creation software 1110 having a first configuration may be operative on the server 1102, and the document creation software 1110 having a second configuration may be operative on one or more of the client computing devices 1106.

Additionally, in various exemplary embodiments, the document creation software 1110 may utilize various input, tracking and/or assessment techniques, methods, and/or technologies in order to facilitate operations on information associated with a patient. For example, the document creation software 1110 may be configured with various graphical user interface components, windows, prompts, menus, buttons, text boxes, data input components, voice recorders, templates, touch screens, digital pens, digital tablets, and/or the like, as desired. Moreover, any input, storage, transmission, and/or output techniques now known or hereafter invented may suitably be used.

The document creation software 1110 is configured to allow data input via multiple channels. In an exemplary embodiment, the document creation software 1110 allows data input by mouse clicks (e.g., clicks to indicate entry of "normals", i.e., default or expected responses to a query, and the like), embedded dictation, input via touch, and/or free text entry. An interface supporting clicking, touching, talking, and/or typing improves user efficiency, for example by allowing the user to move from recording narrative (e.g., a dictation snippet) to clicking normals and back to recording without the need to stop or save midstream. Additionally, this interface allows editing of any element once added to a document. Conceptually, this interface simulates free form dictation, allowing the user to dictate quickly from element to element. Additionally, the interface and/or templates may be modified, as desired, for example to support custom normals. In this manner, dictation of often repeated normals may be reduced and/or eliminated.

Moreover, in various exemplary embodiments, the document creation software 1110 is configured to support use of a digital pen and paper. For example, a physician may utilize a digital pen to initiate a new document session and note normals at the bedside in order to increase quality time with a patient. Resulting data may suitably be transferred from the digital pen to the document creation software 1110 via any suitable method, for example in a wireless manner via Bluetooth or Wi-Fi. In this manner, physician time spent at the computer may be reduced, as a digital document may be pre-populated with data for normals, notes for referral, and/or the like, reducing the amount of computer time needed to complete documentation during and/or after a patient visit.

The document creation software 1110 may be configured to support dictation. In various exemplary embodiments, the document creation software 1110 may be configured to support recording, transcription, retrieval, and/or any other desired operations on dictation snippets (for example, dictation snippets pertaining to a single portion of a template within the document creation software 1110). When recorded, dictation snippets may be immediately transferred to a database associated with the document creation software 1110, reducing the risk of data corruption or loss. In contrast, in freeform dictation, audio is often only saved after completion of the entire audio record, resulting in more frequent information loss due to the extended time between saves.

The document creation software 1110 may be further configured to support parallel processing of dictation snippets. In various exemplary embodiments, a user of the document creation software 1110 may input multiple dictation snippets in connection with an event, for example a clinical interview with a patient. Because each dictation snippet may be stored and/or processed individually, a particular snippet may be uploaded and delivered for transcription immediately, rather than waiting for additional snippets associated with the same document session. Moreover, dictation snippets from one documentation session may be separated and delivered to many transcriptionists in a parallel fashion, reducing transcription turn-around time.

Additionally, because dictation snippets may be separated as desired, particular dictation snippets needing increased oversight and/or security (e.g., dictation snippets containing personally identifiable information, and the like) may be processed in a first manner, and other dictation snippets needing less oversight and/or security (e.g., dictation snippets containing general information, diagnostic information, and/or the like) may be processed in a second manner different from the first manner. In an exemplary embodiment, each dictation snippet is indexed by a document session ID and a dictation ID. Thus, the dictation snippet may not be directly relatable to a physician and/or a patient. Moreover, dictation snippets may be configured to not carry patient health information. This de-identification of a dictation snippet may allow for secure transfer of dictation to transcriptionists or other service providers, and can result in additional cost savings and/or enhanced patient and physician confidentiality and/or privacy.

Further, in various exemplary embodiments, the document creation software 1110 may be configured to link dictation snippets within a document where they were placed by a system user. Moreover, these dictation snippets may be stored with a finalized document in perpetuity. Linking the documentation snippets in-line with document content can create a more complete document to be entered into the patient record. Additionally, the original words, narrative, and/or intent of the author may be better preserved by keeping dictation snippets embedded within the finalized (and fully transcribed) document.

In certain exemplary embodiments, the document creation software 1110 is configured with a built-in transcription module. In this manner, audio data may be integrated into a document. For example, dictation snippets captured by a recorder of the document creation and management system 1100 may be transcribed, and the resulting text may be integrated into a particular location within a document, for example a location defined by a template. Transcription may be performed by any suitable entity, at any suitable location, and/or at any suitable time, as desired. For example, a dictation snippet may be stored, and later transcribed by the individual who created the dictation, for example a physician. Moreover, a dictation snippet may be transcribed by a physicians' staff member, an external transcription service provider, and/or a provider of the document creation and management system, as desired. For example, a provider of the document creation software 1110 may also offer transcription services in order to offer a physician a one-stop digital documentation solution, reducing the risk of data breaches or other unauthorized or undesired access to patient information.

Moreover, in certain embodiments, the document creation software 1110 may be configured with speech recognition capability, allowing instant transcription of dictation snippets. For example, a user may utilize audio capture capabilities of the document creation software 1110 to store dictation. Audio information captured by the document creation software 1110 may be immediately delivered to a speech recognition module, and the resulting automated transcription may be stored and/or displayed, as desired. Moreover, speech recognition capability may be implemented at any suitable location within a document creation and management system 1100, for example on the client computing devices 1106, on the server 1102, and so forth.

Additionally, transcription workflow within the document creation software 1110 may be customized and/or otherwise configured for a particular system user. In various exemplary embodiments, default transcription workflow for a particular customer may be defined in a customer profile; however, default transcription workflow behavior may also be modified on the fly, e.g., on a document-by-document basis, on a patient-by-patient basis, and/or the like. Moreover, the document creation software 1110 may be configured with standard transcription functionality and/or features (e.g., fast forward, reverse, playback speed adjustment, and/or the like). The document creation software 1110 may be further configured to allow use of a transcription foot pedal or other external assistive devices.

In various exemplary embodiments, the document creation software 1110 may comprise a template driven platform. For example, an author-specific menu system with predefined normals may be provided, driven by a rich text document template. The template may be created using any suitable word processing software (e.g., Microsoft Word, OpenOffice, and/or the like). Moreover, the template may be created by a physician or other user of the document creation software 1110. The template may also be created by a provider of the document creation and management system 1100 (and/or document creation software 1110), and/or a third party, as desired. Multiple templates may be integrated into the document creation and management system 1100. For example, additional templates may be uploaded and/or made available to a particular user of the document creation software 1110. Moreover, a template may be privately stored (e.g., it may be configured for use by a particular physician, practice group, office, and/or the like); alternatively, a template may be available to multiple users of the document creation software 1110.

In certain exemplary embodiments, the document creation software 1110 is configured to provide tracking of document creation in order to help guide a system user to reduce mistakes, correlate related information, and/or to highlight opportunities to document important information. Additionally, the document creation software 1110 is configured to utilize the E&M Guidelines in order to assist a system user to accurately document the level of E&M service performed. In this manner, the document creation software 1110 increases reimbursement opportunities for a physician.

The document creation software 1110 may also be configured with various components configured to reduce a risk of data loss. For example, in various exemplary embodiments, the document creation software 1110 is configured with an auto-save function. Any action and/or every action by a user may trigger the auto-save function. Once activated, the auto-save function may upload and/or store the most recent changes to the document to the database in real-time. In this manner, risk of data loss may be minimized.

The document creation software 1110 allows review of any and all documents created. In various exemplary embodiments, during a creation of a document, a system user may be provided with the complete patient history for individual elements of a document. A history function allows the user to access the patient history, for example to aid in recall of previously created documents, to generate and/or refine a diagnosis in light of historical events, and/or the like. Additionally, the history function of the document creation software 1110 may allow a user to populate at least a portion of the current document with information from previously generated documents. In this manner, redundant actions may be reduced and accuracy may be improved, because there is no need to re-enter information documented during a previous document session.

In certain exemplary embodiments, the document creation software 1110 is configured to support assessment, analysis, and/or other actions on data. For example, the document creation software 1110 may be configured to support data mining. Each document entry may be stored by category and/or sub-element type (for example, as defined by a document template). Categories and/or sub-element types may be individually data mined to provide detailed information, summary information, and/or statistical data to a system user or third party.

The document creation software 1110 may also interface with other systems, software products, and/or the like. In an exemplary embodiment, the document creation software 1110 may be configured to be compatible with Health Level 7 (HL7) communication standards, for example standards related to Admission Discharge and Transfer (ADT) messages in order to allow communication between the document creation software 1110 and other electronic record systems, hospital administration systems, scheduling systems, database management systems, and/or the like. Moreover, the document creation software 1110 may communicate with any other desired electronic systems, for example across the network 1104. In this manner, integration of the document creation software 1110 with existing software products, for example integrating the document creation software 1110 with a hospital electronic medical record (EMR) system, may be easily accomplished.

In certain exemplary embodiments, the document creation and management system 1100 is configured to be suitable for use by multiple individuals and/or users having varied levels of access to data, as described above with reference to FIGS. 7A and 7B.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a tangible computer-readable storage medium having computer-readable program code means embodied in the storage medium. Any suitable computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture including instruction means which implement the function specified. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The foregoing specification has been described with reference to various embodiments. However, one of ordinary skill in the art appreciates that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection.

What is claimed is:

1. A document creation and management system comprising:

an input subsystem to receive input from a given user via one or more input devices to generate content of a document, the content comprising one or more discrete entries, the input subsystem including a processor to receive the input and compose the input as an entry of the content of the document, the input subsystem comprising:

a navigator component presenting, on a display, prompts and corresponding input controls organized according to a predefined template, the prompts and corresponding input controls to guide collection of input and guide composing of the one or more discrete entries to create the content of the document, wherein the predefined template comprises formatting rules defined by the given user;

an auto-insertion component to compose preconfigured data into an entry in response to activation of a click input control;

a recorder to record input to compose into an entry in response to activation of a record input control; and a composer configured to receive and compose data into an entry in response to activation of a type input control;

a document creation subsystem configured to generate the document using the one or more discrete entries composed by the input subsystem; and a document storage subsystem configured to store the document on a nontransitory computer readable storage medium, wherein the document is stored as an association of the one or more discrete entries.

2. The document creation and management system of claim 1, wherein the composer is further configured to present a second click input control and compose preconfigured data into an entry in response to activation of the second click input control and further configured to present a second record input control to activate the recorder to record input and to compose the recorded input into an entry in response to activation of the second record input control.

3. The document creation and management system of claim 1, wherein the auto-insertion component is further configured to also compose preconfigured data into an entry in response to activation of a touch input control.

4. The document creation and management system of claim 1, wherein the document creation subsystem is further configured to manage and automate processing of the one or more discrete entries of the document by automatically sending the one or more discrete entries to an external processing subsystem, wherein processing includes one or more of transcription, editing, coding, encrypting, speech recognition and optical character recognition.

5. The document creation and management system of claim 1, further comprising a processing subsystem configured to process the one or more discrete entries of the document, wherein the document creation subsystem manages processing of the one or more discrete entries of the document by sending the one or more discrete entries to the processing subsystem.

6. The document creation and management system of claim 5, wherein the processing subsystem comprises speech recognition to transcribe spoken audio input to text, and wherein the document creation subsystem receives the transcribed text of the audio input and composes the text into an entry of the document at an appropriate position in the content of the document.

7. The document creation and management system of claim 1, wherein the navigator component of the graphical user interface of the input subsystem orders the prompts and corresponding input controls according to rules of the predefined template.

8. The document creation and management system of claim 7, wherein the predefined template outlines a structure of the document, including an arrangement of the one or more discrete entries and outlining a structure of the one or more discrete entries to be composed to populate the content of the document, the arrangement of the one or more discrete entries comprising one or more of ordering and formatting.

9. The document creation and management system of claim 8, wherein the predefined template is customized to mirror a document creation thought process of the given user creating the document.

10. The document creation and management system of claim 1, wherein the input subsystem further comprises a viewer to display in real-time the contents of the document according to formatting as an output document.

11. The document creation and management system of claim 1, wherein, after the input subsystem composes each entry of the document, the document creation subsystem produces an output document and the document storage subsystem stores the output document.

12. The document creation and management system of claim 1, wherein the input subsystem comprises a web server configured to serve a graphical user interface of the subsystem over a network to a client computer for viewing in a web browser and to receive input from the client computer via the network.

13. The document creation and management system of claim 1, wherein the recorder records audio.

14. The document creation and management system of claim 1, wherein the recorder records video.

15. The document creation and management system of claim 1, wherein the recorder records output of a monitoring system.

16. A document creation and management system comprising:
    a processor;
    a display in communication with the processor;
    a plurality of input devices in communication with the processor, the plurality of input devices including at least a keyboard and a microphone;
    a memory in communication with the processor, the memory comprising:
        an input subsystem module to receive input from a given user via the plurality of input devices to generate the content of a document, the content comprising one or more discrete entries, the input subsystem to present on the display a graphical user interface configured to receive the input and compose the input into an entry of the content of the document, the graphical user interface comprising:
            a navigator component presenting prompts and corresponding input controls organized according to a predefined template, the prompts and corresponding input controls to guide collection of input and guide composing of entries to create the content of the document, wherein the template comprises formatting rules defined by the given user, the input controls including a record input control and a type input control;
            a recorder to record input to compose into an entry in response to activation of the record input control; and
            a composer configured to receive data to compose the data into an entry in response to activation of the type input control;
    a document creation subsystem configured to generate the document using the one or more discrete entries created by the input subsystem; and
    a document storage subsystem configured to store the document, wherein the document is stored as the one or more discrete entries stored associated together.

17. The document creation and management system of claim 16, wherein the navigator further comprises an auto-insertion component to compose preconfigured data into an entry in response to activation of a click input control.

18. The document creation and management system of claim 1, wherein the composer is further configured to present a second click input control and compose preconfigured data into an entry in response to activation of the second click input control and further configured to present a second record input control to activate the recorder to record input and to compose the recorded input into an entry in response to activation of the second record input control.

19. The document creation and management system of claim 16, further comprising a processing subsystem configured to process the one or more discrete entries of the document, wherein the document creation subsystem manages processing of the one or more discrete entries of the document by sending the one or more discrete entries to the processing subsystem.

20. A method of document creation and management comprising:
receiving input via one or more input devices to generate the content of a document, the content comprising one or more discrete entries, receiving input comprising:
presenting a navigator component having prompts and corresponding input controls organized according to a predefined template, the prompts and corresponding input controls to guide collection of input to create the content of the document, wherein the predefined template comprises formatting rules defined by the given user;
recording input in response to activation of a record input control; and
receiving typed data into an entry in response to activation of a type input control;
composing the received input as an entry of the content of the document,
storing the document as an association of discretely stored entries.

21. The method of claim 20, wherein receiving input further comprises inserting preconfigured data into an entry in response to activation of a click input control.

22. The method of claim 20, further comprising processing entries of the document by sending the entries to a processing subsystem.

23. The method of claim 20, wherein the processing entries further comprises receiving back from the processing subsystem processed data and associating the processed data with a corresponding document entry previously sent for processing.

24. The method of claim 20, further comprising presenting in real-time the contents of the document according to formatting rules as an output document.

25. The method of claim 20, wherein the navigator component orders the presentation of the prompts and corresponding input controls according to a predefined template.

26. A non-transitory computer readable storage medium having recorded thereon instructions that, if executed by a computer, cause the computer to perform a method of document creation and management, the method comprising:
receiving input via one or more input devices to generate the content of a document, the content comprising one or more discrete entries, receiving input comprising:
presenting a navigator component having prompts and corresponding input controls organized according to a predefined template, the prompts and corresponding input controls to guide collection of input to create the content of the document, wherein the template comprises formatting rules defined by the given user;
recording input in response to activation of a record input control; and
receiving typed text into an entry in response to activation of a type input control;
composing the received input as an entry of the content of the document; and
storing the document as an association of discretely stored entries.

27. A document creation and management system comprising:
a plurality of input devices to enable input by a given user;
a display to present a graphical user interface to a user;
an input subsystem to receive input via the plurality of input devices to generate content of a document, the content comprising one or more discrete entries, the input subsystem to receive the input and compose the input as an entry of the content of the document, the input subsystem comprising:
a navigator component presenting, on the display, prompts and corresponding input controls organized according to a predefined template that is customizable by the given user, the prompts and corresponding input controls to guide collection of input to create the content of the document, wherein the predefined template comprises formatting rules defined by the given user;
a document creation subsystem configured to generate the document using entries composed by the input subsystem; and
a document storage subsystem configured to store the document on a computer readable storage medium, wherein the document is stored as an association of the one or more discrete entries.

* * * * *